United States Patent [19]

Lippman et al.

[11] 4,244,966
[45] Jan. 13, 1981

[54] 1,3-DIHYDRO-3-(2-HYDROXY-, 2-BROMO- OR 2-CHLOROETHYL)-2H-ISOINDOL-1-ONE DERIVATIVES

[75] Inventors: Wilbur Lippman, St. Laurent; Christopher A. Demerson, Montreal; Leslie G. Humber, Dollard des Ormeaux; Jean-Marie Ferland, St. Laurent, all of Canada

[73] Assignee: American Home Products Corporation, New York, N.Y.

[21] Appl. No.: 78,546

[22] Filed: Sep. 24, 1979

[51] Int. Cl.$^3$ .................. A61K 31/40; C07D 209/46
[52] U.S. Cl. .................. 424/274; 260/325 PH
[58] Field of Search .................. 260/325 PH; 424/274

[56] References Cited

U.S. PATENT DOCUMENTS 3,892,771  7/1975  Eberle .................. 260/326.1

OTHER PUBLICATIONS

H. J. Roth et al., Arch. Pharm., 309, 58 (1976).
Derwent Publications Ltd., Farmdoc 21903V for Japanese Patent J49014459.
Chem. Abst. 78:58179S (1973) for Tetra. Letters, 4517 (1972).
Chem. Abst. 55:15485c (1961) for Gazz. chim. ital., 90559 (1960).
E. Breuer et al., Tetrahedron, 31, 499 (1975).
F. M. Rowe et al., J. Chem. Soc. 1098 (1936).
Chem. Abstracts 80:108372p (1974), Abstract of Japanese Kokai, 74 14,459.
Chem. Abstracts 85:46384m (1976).
H. Roth et al., Arch. Pharm. 309 pp. 58 et seq. (1976).

*Primary Examiner*—Donald G. Daus
*Assistant Examiner*—M. C. Eakin
*Attorney, Agent, or Firm*—Arthur E. Wilfond

[57] ABSTRACT

Derivatives of 1,3-dihydro-3-(2-hydroxyethyl) -2H-isoindol-1-one are disclosed. The derivatives are useful for treating ulcers in a mammal and for preventing or decreasing the secretion or availability of excessive amounts of gastric or hydrochloric acid in a mammal suffering from hyperchlorhydria and/or associated conditions.

21 Claims, No Drawings

1,3-DIHYDRO-3-(2-HYDROXY-, 2-BROMO- OR 2-CHLOROETHYL)-2H-ISOINDOL-1-ONE DERIVATIVES

RELATED CASES

Some of the compounds of this invention are disclosed as intermediates for the production of TRICYCLIC ISOINDOLE DERIVATIVE in Ser. No. 78,547 of Christopher A. Demerson, Jean-Marie Ferland and Leslie G. Humber, filed on even date herewith. Application Ser. No. 78,548 of Wilbur Lippmann, METHOD OF USE AND COMPOSITION FOR 1,3-DIHYDRO-3-(2-HYDROXY-2-METHYL-PROPYL)-2H-ISOINDOL-1-ONE, filed on even date herewith is also related hereto. 1,3-Dihydro-3-(2-hydroxyethyl)-2H-isoindol-1-one is referred to as 2,3-dihydro-3-(2-hydroxyethyl)-1H-isoindol-1-one in Example 37 of 78547.

BACKGROUND OF INVENTION (a) Field of the Invention

This invention relates to novel 1,3dihydro-3-(2-hydroxyethyl)-2H-isoindol-1-one derivatives, to processes for their preparation, to methods of using the derivatives and to pharmaceutical compositions of the derivatives. These compounds are useful for treating ulcers in a mammal and for preventing or decreasing the secretion or availability of excessive amounts of gastric or hydrochloric acid in a mammal suffering from hyperchlorhydria and/or associated conditions.

(b) Description of the Prior Art

A search of the chemical literature of 3-substituted derivatives of 1,3-dihydro-2H-isoindol-1-one has revealed the following references: H. J. Roth and G. Hundeskagen, Arch. Pharm. 309, 58 (1976); Derwent Publications Ltd. Farmdoc 21903 v for Japan Patent J4 9014,459; Chem. Abstr., 78, 58179s (1973) for Tetrahedron Lett., 4517 (1972); M. K. Eberle, U.S. Pat. No. 3,892,771, issued July 1, 1975; E. Breuer and S. Zbaida, Tetrahedron, 31, 499 (1975); and Chem. Abstr., 55, 15485c (1961) for Gazz. chim. ital., 90, 559 (1960). Although the above references disclose a number of 3-substituted 2,3-dihydro-1H-isoindol-1-one compounds, they do not reveal any 3-(2-hydroxyethyl) derivatives, which are related to the 1,3-dihydro-3-(2-hydroxyethyl)-2H-isoindol-1-one derivatives of this invention. F. M. Rowe et al., J. Chem. Soc. 1098 (1936) describes a process, which we have modified to produce some compounds of this invention.

SUMMARY OF INVENTION

As aspect of this invention involves pharmaceutical compositions and methods using a compound of formula I

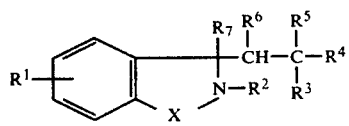

in which $R^1$ represents one or two substituents on the aromatic ring selected from hydrogen, lower alkyl, lower alkoxy, halo or trifluoromethyl; $R^2$ is hydrogen, lower alkyl or carboxymethyl; $R^3$ is hydrogen, lower alkyl or phenyl; $R^4$ is lower alkyl or phenyl; $R^5$ is bromo, chloro or hydroxy; $R^6$ is hydrogen or lower alkyl; $R^7$ is hydrogen or methyl and x is C=O; with the proviso that when $R^1$, $R^2$, $R^6$ and $R^7$ are hydrogen, $R^3$ and $R^4$ are methyl and X is C=O, then $r^5$ is bromo or chloro.

A preferred group of compounds of formula I for pharmaceutical compositions and methods of use is one in which $R^1$ represents one or two substituents on the aromatic ring selected from hydrogen, lower alkyl, lower alkoxy or halo; $R^2$ is hydrogen, lower alkyl or carboxymethyl; $R^3$ is hydrogen, lower alkyl or phenyl; $R^4$ is lower alkyl or phenyl; $R^5$ is bromo, chloro or hydroxy; $R^6$ is hydrogen or lower alkyl; $R^7$ is hydrogen or methyl and x is C=O; with the proviso that when $R^1$, $R^2$, $R^6$ and $R^7$ are hydrogen, $R^3$ and $R^4$ are methyl and X is C=O, then $R^5$ is bromo or chloro.

A more preferred group of compounds of formula I for pharmaceutical compositions and methods of use is one in which $R^1$ represents one or two substituents on the aromatic ring selected from hydrogen or halo; $R^2$, $R^6$ and $R^7$ are hydrogen; $R^3$ is hydrogen or lower alkyl having one to three carbon atoms; $R^4$ is lower alkyl having one to three carbon atoms; $R^5$ is chloro or hydroxy and X is C=O; with the proviso that when $R^1$, $R^2$, $R^6$ and $R^7$ are hydrogen and $R^3$ and $R^4$ are methyl, then $R^5$ is chloro.

A compound of formula I, as described above, is useful for treating ulcers in a mammal by administering to the mammal an effective ulcer alleviating amount of the latter compound of formula I. A compound of formula I, as described above, is also useful for preventing or decreasing the secretion or availability of excessive amounts to gastric acid, and hydrochloric acid, in a mammal, which comprises administering to the mammal suffering from hyperchlorhydria and/or associated conditions an effective amount of the compound of formula I. The compound of formula I is administered orally or parenterally.

A pharmaceutical composition for oral or parenteral administration is provided by combining the compound of formula I with a suitable pharmaceutically acceptable carrier.

Another aspect of this invention involves the compounds of formula I

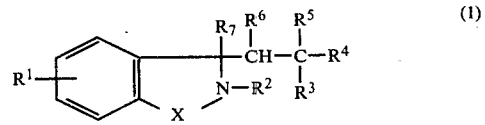

in which $R^1$ represents one or two substituents on the aromatic ring selected from hydrogen, lower alkyl, lower alkoxy, halo or trifluoromethyl; $R^2$ is hydrogen, lower alkyl or carboxymethyl; $R^3$ is hydrogen, lower alkyl or phenyl; $R^4$ is lower alkyl or phenyl; $R^5$ is bromo, chloro or hydroxy; $R^6$ is hydrogen or lower alkyl; $R^7$ is hydrogen or methyl and X is C=O, with the proviso that when $R^1$ represents one or two substituents at positions 5 and 6 on the aromatic ring; $R^2$, $R^6$ and $R^7$ are hydrogen; $R^3$ is hydrogen or lower alkyl and $R^4$ is lower alky; then $R^5$ is bromo or chloro.

A preferred group of compounds of formula I is one in which $R^1$ represents one or two substituents on the aromatic ring selected from hydrogen, lower alkyl, lower alkoxy or halo; $R^2$ is hydrogen, lower alkyl or carboxymethyl; $R^3$ is hydrogen, lower alkyl or phenyl; $R^4$ is lower alkyl or phenyl; $R^5$ is bromo, chloro or hydroxy; $R^6$ is hydrogen or lower alkyl; $R^7$ is hydrogen or methyl and X is C=O; with the proviso that when $R^1$ represents one or two substituents at positions 5 and 6 on the aromatic ring; $R^2$, $R^6$ and $R^7$ are hydrogen; $R^3$ is hydrogen or lower alkyl and $R^4$ is lower alkyl; then $R^5$ is bromo or chloro.

A more preferred group of compounds of formula I is one in which $R^1$ represents one or two substituents on the aromatic ring selected from hydrogen or halo; $R^2$, $R^6$ and $R^7$ are hydrogen; $R^3$ is hydrogen or lower alkyl having one to three carbon atoms; $R^4$ is lower alkyl having one to three carbon atoms; $R^5$ is chloro or hydroxy and X is C=O; with the proviso that when $R^1$ represents one or two substituents at positions 5 and 6 then $R^5$ is chloro.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, isopropyl, butyl, isobutyl, pentyl, hexyl and the like.

The term "halo" as used herein means halogens and includes fluorine, chlorine, bromine and iodine, unless stated otherwise.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexyloxy and the like.

The term "lower alkanol" as used herein means both straight and branched chain alkanols containing from one to six carbon atoms and includes methanol, ethanol, isopropanol, butanol, hexanol and the like.

When a compound of formula I is administered to a mammal suffering from hyperchlorhydria and/or associated conditions for the purpose of preventing or decreasing the secretion of excessive amounts of gastric acid or hydrochloric acid or is used for the treatment of ulcers in a mammal, it is used alone or in combination with pharmacologically acceptable carriers, the proportion of which is determined by the solubility and chemical nature of the compound, chosen route of administration and standard biological practice. For example, it is administered orally in solid form, i.e. capsule or tablet, orally in liquid form, i.e. suspensions or solutions, or it can be injected parenterally. The preferred method of administration is oral.

The tablet compositions contain a compound of formula I in admixture with nontoxic pharmaceutical excipients such as for example, starch, milk-sugar, certain types of clay and so forth. The tablets can be uncoated or they can be coated by known techniques so as to delay disintegration and adsorption in the gastrointestinal tract and thereby provide a sustained action over a longer period.

The aqueous suspensions for oral administration contain a compound of formula I in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions for oral administration can be formulated by suspending the compound in a vegetable oil, for example, arachis oil, olive oil, sesame oil, or coconut oil or in a mineral oil, for example, liquid paraffin, and the suspension may contain a thickening agent, for example, beeswax, hard paraffin or cetyl alcohol. The compositions can also contain a sweetening agent, flavoring agent or antioxidant.

For administration to a mammal by parenteral injection, it is preferred to use a compound of formula I in solution in a sterile aqueous vehicle, which may also contain other solutes such as buffers or preservatives, as well as sufficient quantities of pharmaceutically acceptable salts or of glucose to make the solution isotonic.

The dosage of a compound of formula I for combating or preventing hyperchlorhydria, and/or associated conditions, or for the treatment of ulcers in a mammal will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under circumstances is reached. In general, the compound is most desirably administered at a concentration level that will generally afford effective results without causing any harmful or deleterious side effects. For example, an effective anti-ulcer amount or an effective amount for preventing hyperchlorhydria and inhibiting gastric or hydrochloric acid secretion of a compound of formula I usually ranges from about 1.0 mg to about 200 mg per kg of body weight per day in single or divided dose when administered orally, although as aforementioned, variations will occur. However, a dosage level that is in the range from about 10 mg to about 100 mg per kg of body weight per day in single or divided dose when administered orally is employed most desirably in order to achieve effective results.

The effectiveness of the compounds of formula I as agents for preventing hyperchlorhydria and inhibiting hydrochloric acid secretion is demonstrated by the use of rats, more especially the Shay rat. The rat is the preferred experimental mammal for demonstrating the activity of agents affecting gastric acid secretion and it has been widely used in experimental medicine for this purpose. For instance, on page 149 in "Pathophysiology of Peptic Ulcer", published by McGill University Press, Montreal, Canada in 1963, Skoryna states that many of the drugs now in use in human medicine for the treatment of peptic ulcer have been evaluated by the Shay rat method. It is recognized by skilled pharmacologists that results obtained in the Shay rat in the evaluation of gastric acid conditions are translatable to results that will be obtained when the same drug is administered to human beings. For the value of the Shay rat in experimental gastroenterology, see also the article by H. Shay et al., Gastroenterology, 26, 906 (1954). This animal is generally recognized as the preferred, or standard, animal for use experimentally in testing drugs used to inhibit gastric acid secretion.

The compounds of formula I are shown to be useful for treating ulcers in a mammal by inhibiting basal gastric acid secretion in the rat, as described above, and inhibiting indomethacin-induced ulcer formation in the rat according to the method described by Y. H Lee et al., Arch. Int. Pharmacodyn. Ther., 191, 370 (1971) and cold-resistant-induced ucler formation in the rat according to the method described by D. A. Brodie and L. S. Valitski, Proc. Soc. Exp. Biol Med., 113, 998 (1963) as modified by E. C. Senay and R. J. Levine, Proc. Soc. Biol. Med., 124, 1221 (1967) when administered orally or parenterally. Compounds, which exhibit activity in the above anti-ulcer or anti-secretory tests, are regarded as anti-ulcer agents.

With regard to the formation of ulcers caused by indomethacin, breakdown of mucosal resistance has been suggested to be of importance, see R. Menguy and L. Desbaillets, Amer. J. Dig. Dis., 12, 862 (1976) and D. M. Nicoloff, Arch Surg., 97, 809 (1968). Furthermore, a possible role of the vagus was considered, see Y. H. Lee et al., Arch. Int. Pharmacodyn. Ther., 191 370 (1971). Indomethacin induces ulcer formation, while having no effect on gastric acid secretion (Lee et al., cited above). Although the production of excess gastric acid does not appear to be the mechanism by which indomethacin causes ulcer formation, it is probable that in the presence of a reduced mucosal resistance, gastric acid plays an important role in the ulcer formation. As the compounds of formula I can inhibit gastric acid secretion, it is this type of action that can be significant in the prevention of ulcer formation.

Anticholinergic agents are known to exhibit gastric acid antisecretory and antiulcer activities in the rat, see J. M. Beiler et al., Arch. Int. Pharmacodyn., 153, 139 (1965); W. Lippmann, Prostaglandins, 7, 1(1974); and A. Robert et al., Digestion, 11, 199 (1974), and are widely employed clinically as antisecretory-antiulcer agents; however, such agents exhibit various side effects, see D. W. Piper et al., Drugs 10 56 (1975). In this regard, the compounds of formula I do not exhibit appreciable anticholinergic activity. Accordingly, the lack of this latter activity for the compounds of formula I is a desirable feature of these compounds.

PROCESS

The compounds of formula I, as well as related compounds wherein X is $SO_2$ or $CH_2$, are prepared from a variety of intermediates which are either knon or can be prepared by known procedures.

One series of intermediates is illustrated in reaction scheme 1.

REACTION SCHEME 1

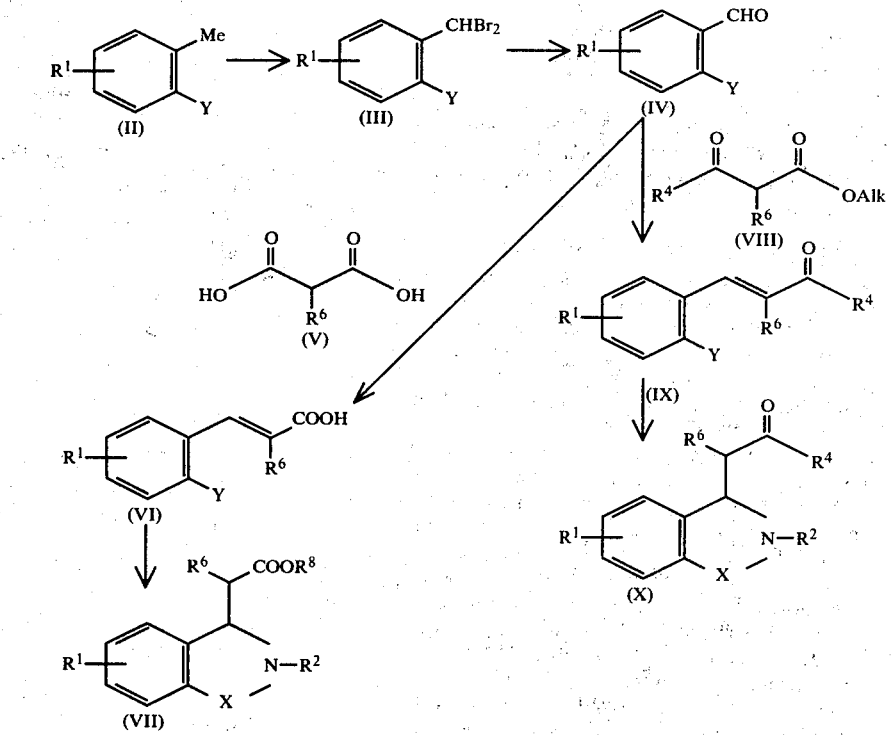

With reference to reaction scheme 1, a toluene derivative of formula II in which $R^1$ is as defined herein and Y is CN or $SO_3$ Na is reacted with two to three molar equivalents of N-bromosuccinimide in carbon tetrachloride at 50° to 80° C. while irradiating with a 500 W lamp for six to ten hours to obtain the corresponding dibromomethyl compound of formula III in which $R^1$ and Y are as defined herein.

Reaction of the compound of formula III with two to four molar equivalents of silver nitrate in 95% ethanol at 50° to 80° C. for two to ten hours affords the corresponding benzaldehyde of formula IV in which $R^1$ and Y are as defined herein.

Condensation of the latter compound with 1.5 to 4 molar equivalents of a malonic acid derivative of formula V in which $R^6$ is as defined herein in the presence of two to three molar equivalents of piperidine in pyridine at 80° to 120° C. for one to five hours gives the corresponding compound of formula VI in which $R^1$, $R^6$ and Y are as defined herein.

Cyclization of the latter compound with an aqueous solution of 5 to 20% sodium or potassium hydroxide at 80° to 100° C. for one to ten hours and followed by acidification of the solution with a mineral acid, e.g. hydrochloric acid or sulfuric acid, affords the corresponding compound of formula VII in which R¹ and R⁶ are as defined herein, R² and R⁸ are hydrogen and X is CO or SO₂. The latter acid is esterified to obtain the corresponding ester of formula VII in which R¹ and R⁶ are as defined herein, R² is hydrogen, R⁸ is lower alkyl and X is CO or SO₂. Most of the standard esterification methods can be used. A preferred method involves the use of a solution of the acid in a lower alkanol and a catalytic amount of p-toluenesulfonic acid at 70° to 80° C. for two to ten hours.

Still with reference to reaction scheme 1, the benzaldehyde of formula IV is condensed with a compound of formula VIII in which R⁴ and R⁶ are as defined herein and Alk is lower alkyl, in the same manner as described above for the condensation of IV plus V to give VI, to obtain the corresponding compound of formula IX in which R¹, R⁴, R⁶ and Y are as defined herein. Cyclization of the latter compound, in the same manner as described above for the cyclization of VI to give VII, affords the corresponding compound of formula X in which R¹, R⁴ and R⁶ are as defined herein, R² is hydrogen and X is CO or SO₂.

If desired, the acidic compound of formula VII in which R¹ and R⁶ are as defined herein, R² and R⁸ are hydrogen and X is CO or SO₂ is reacted with four to six molar equivalents of methyl lithium in tetrahydrofuran at 20° to 30° C. for two to ten hours to obtain the corresponding compound of formula X in which R¹ and R⁶ are as defined herein, R² is hydrogen, R⁴ is methyl and X is CO or SO₂.

If desired, the above described compounds of formula VII, in which R² is hydrogen and R⁸ is lower alkyl, or of formula X, in which R² is hydrogen, is alkylated with about a molar equivalent of a lower alkyl bromide, chloride or iodide and about 1.0 to 1.5 equivalents of sodium hydride in benzene or toluene at 40° to 60° C. for 15 to 30 hours to obtain the corresponding compounds of formula VII, in which R¹ and R⁶ are as defined herein, R² and R⁸ each is lower alkyl and X is CO or SO₂, or of formula X, in which R¹, R⁴ and R⁶ are as defined herein, R² is lower alkyl and x is CO or SO₂.

Another method for preparing the above described compound of formula VI in which R¹ is as described herein, R⁶ is hydrogen and Y is CN is illustrated in reaction scheme 2.

REACTION SCHEME 2

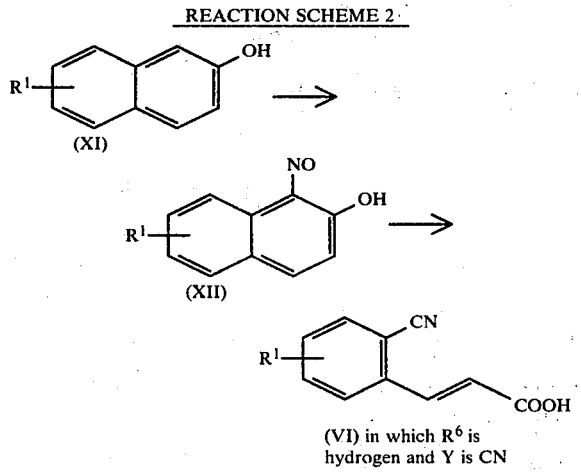

(VI) in which R⁶ is hydrogen and Y is CN

As illustrated in reaction scheme 2, the 2-naphthol or formula XI is reacted with one to three molar equivalents of sodiium nitrite in a solution of aqueous acetic acid at 10° to 30° C. for two to ten hours to obtain the corresponding compound of formula XII in which R¹ is as defined herein. Reaction of the latter compound with about an equivalent amount of p-toluenesulphonyl chloride in acetone while maintaining an alkaline solution by the addition of 10% sodium hydroxide at 50° to 60° C. affords the corresponding compound of formula VI in which R¹ is as defined herein, R⁶ is hydrogen and Y is CN. The sequence of reactions as illustrated in reaction scheme 2 has been described by F. M. Rowe et al., J. Chem. Soc. 1098 (1936).

Another method for preparing the above described compound of formula X in which R¹, R⁴ and R⁶ are as defined herein, R² is hydrogen or lower alkyl and X is CO is illustrated in reaction scheme 3.

REACTION SCHEME 3

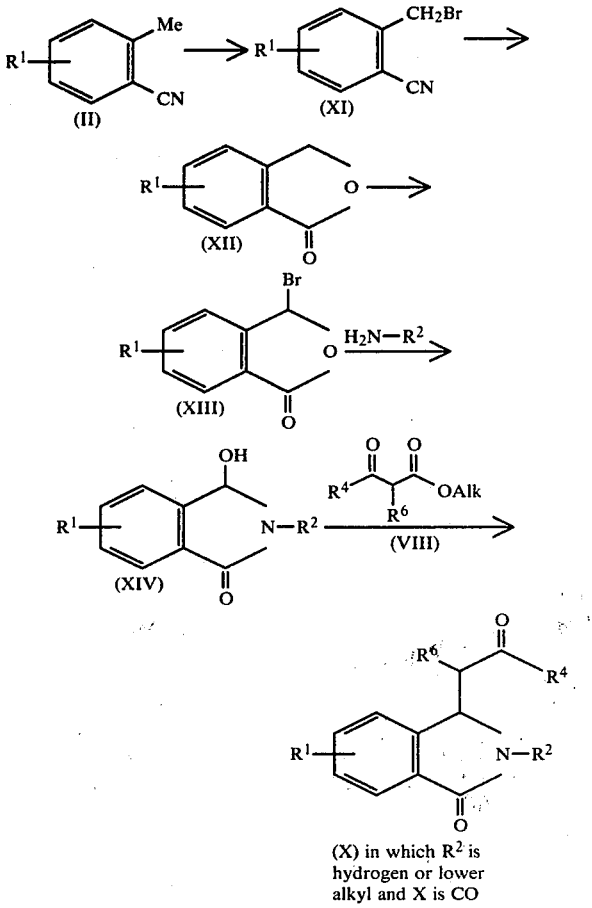

(X) in which R² is hydrogen or lower alkyl and X is CO

With reference to reaction scheme 3, the benzontrile of formula II in which R¹ is as defined herein and Y is CN is reacted with about one to two molar equivalents of N-bromosuccinimide in carbon tetrachloride at 50° to 80° C. while irradiating with a 500 W lamp for two to five hours to obtain the corresponding bromomethyl compound of formula XI in which R¹ is as defined herein. A solution of the latter compound in about 7% nitric acid is heated at 80° to 100° C. for one to five hours to obtain the corresponding compound of formula XII in which R¹ is as defined herein.

Bromination of the latter compound with about a molar equivalent of N-bromosuccinimide in carbon tetrachloride while irradiating with a 500-W lamp for one to three hours gives the corresponding compound of formula XIII in which $R^1$ is as defined herein. The latter compound is reacted with about two to ten molar equivalents of ammonia or a lower alkyl amine of formula $H_2N-R^2$ wherein $R^2$ is lower alkyl in methanol at 20° to 50° C. for 10 to 50 minutes to obtain the corresponding compound of formula XIV in which $R^1$ is as defined herein and $R^2$ is hydrogen or lower alkyl.

Condensation of the latter compound with about 2.5 to 4.0 molar equivalents of a compound of formula VIII in which $R^4$, $R^6$ and Alk are as defined herein in a solvent of concentrated sulfuric acid at 20° to 50° C. for 20 to 80 hours gives the corresponding compound of formula X in which $R^1$, and $R_4$ and $R^6$ are as defined herein, $R^2$ is hydrogen or lower alkyl and X is CO. Such a condensation has been described by A. Warshawsky and D. Ben-Ishai, J. Het. Chem., 7, 917 (1970).

The above described intermediates of formula VII in which $R^6$ is lower alkyl and formula X are readily converted to the compounds of formula I by a variety of reactions.

The first of these reactions involves the reaction of the latter compounds of formulae VII and X with a Grignard reagent. The Grignard reaction of the compound of formula VII in which $R^1$ and $R^6$ are as defined herein, $R^2$ is hydrogen or lower alkyl, $R^8$ is lower alkyl and X is CO or $SO_2$ with about two, preferably 2.1 to 2.2, molar equivalents of a lower alkyl or phenyl magnesium iodide in an inert solvent, preferably tetrahydrofuran or diethyl ether, at 40° to 60° C. for 15 to 30 hours gives the corresponding compound of formula I in which $R^1$ and $R^6$ are as defined herein, $R^2$ is hydrogen or lower alkyl, $R^3$ and $R^4$ are both the same lower alkyl or both phenyl, respectively, $R^5$ is hydroxy, $R^7$ is hydrogen and X is CO or $SO_2$. In a similar amount but using 3.1 to 3.5 molar equivalents of methyl magnesium iodide, the corresponding compound of formula I in which $R^1$ and $R^6$ are as defined herein, $R^2$ is hydrogen or lower alkyl, $R^3$, $R^4$ and $R^7$ are methyl, $R^5$ is hydroxy and X is CO or $SO_2$ is obtained.

Similarly, reaction of the compound of formula X with 1.1 to 1.3 molar equivalents of a lower alkyl or phenyl magnesium iodide gives the corresponding compound of formula I in which $R^1$, $R^4$ and $R^6$ are as defined herein, $R^2$ is hydrogen or lower alkyl, $R^3$ is lower alkyl or phenyl, $R^5$ is hydroxy. $R^7$ is hydrogen and X is CO or $SO_2$. A similar Grignard reaction of the compound of formula X with 2.1 to 2.5 molar equivalents of methyl magnesium iodide affords the corresponding compound of formula I in which $R^1$, $R^4$ and $R^6$ are as defined herein, $R^2$ is hydrogen or lower alkyl, $R^3$ and $R^7$ are methyl, $R^5$ is hydroxy and X is CO or $SO_2$.

Reduction of the compound of formula X in which $R^1$, $R^4$ and $R^6$ are as defined herein, $R^2$ is hydrogen or lower alkyl and X is CO or $SO_2$ with four to eight molar equivalents of sodium borohydride in ethanol at 50° to 80° C. for 0.5 to 3 hours gives the corresponding compound of formula I in which $R^1$, $R^4$ and $R^6$ are as defined herein, $R^2$ is hydrogen or lower alkyl, $R^3$ is hydrogen, $R^5$ is hydroxy and X is CO or $SO_2$.

Introduction of the methyl group, the methyl as represented by $R^7$, into the above described compounds of formula I in which $R^1$, $R^4$ and $R^6$ are as defined herein, $R^2$ is hydrogen or lower alkyl, $R^3$ is hydrogen, $R^5$ is hydroxy, $R^7$ is hydrogen and X is CO or $SO_2$ requires protection of the hydroxy group. This protection is readily achieved by any of the usual hydroxy protecting groups, such as acetate, benzyl or t-butyl. This intermediate having the protected hydroxy is reacted with the Grignard reagent, methyl magnesium iodide, in the same manner as described above, and the hydroxy protecting group is removed in the usual manner to obtain the corresponding compound of formula I in which $R^1$, $R^4$ and $R^6$ are as defined herein, $R^2$ is hydrogen or lower alkyl, $R^3$ is hydrogen, $R^5$ is hydroxy, $R^7$ is methyl and X is CO or $SO_2$.

Another transformation of the above described compounds of formula I in which $R^1$, $R^3$, $R^4$ and $R^7$ are as defined herein, $R^2$ is hydrogen or lower alkyl, $R^5$ is hydroxy, $R^6$ is hydrogen and X is CO or $SO_2$ involves dehydration of the latter compound with a solution of concentrated sulfuric acid and acetic acid at 30° to 80° C. for one to three hours to obtain the corresponding compound of formula I in which $R^1$, $R^2$, $R^3$, $R^4$, $R^7$ and X are as defined immediately above and $R^5$ and $R^6$ together form a double bond.

Reduction of the compounds of formula I in which $R^1$, $R^3$, $R^4$, $R^6$ and $R^7$ are as defined herein, $R^2$ is hydrogen or lower alkyl, $R^5$ is hydroxy, or $R^5$ and $R^6$ together form a double bond, and X is CO with four to seven molar equivalents of diborane in tetrahydrofuran at 50° to 65° C. for 0.5 to 5 hours, gives the corresponding compound of formula I in which $R^1$, $R^2$, $R^3$, $R^4$, $R^5$, $R^6$ and $R^7$ are as defined immediately above and X is $CH_2$.

Reaction of the compounds of formula I in which $R^1$, $R^3$, $R^4$, $R^6$, $R^7$ and X are as defined herein, $R^2$ is hydrogen and $R^5$ is hydroxy or $R^5$ and $R^6$ together form a double bond with 1.1 to 1.5 molar equivalents of ethyl bromoacetate in the presence of about a molar equivalent of sodium hydride in N,N-dimethylformamide at 20° to 60° C. for two to ten hours affords the corresponding intermediate having an 2-ethoxy-2-oxoethyl group on the nitrogen of the bicyclic ring system. Alkaline hydrolysis of this intermediate with three to five molar equivalents of sodium hydroxide in aqueous ethanol at 20° to 40° C. for 10 to 60 minutes gives the corresponding compound of formula I in which $R^1$, $R^3$, $R^4$, $R^5$, $R^6$, $R^7$ and X are as defined immediately above and $R^2$ is carboxymethyl.

Still another transformation of the above described compounds of formula I in which $R^1$, $R^3$, $R^4$, $R^6$, $R^7$ and X are as defined herein, $R^2$ is hydrogen, or lower alkyl and $R^5$ is hydroxy is the bromination or chlorination of the latter compound with 5 to 20 molar equivalents of thionyl bromide or chloride at 20° to 30° C. for one to ten hours to obtain the corresponding compound of formula I in which $R^1$, $R^2$, $R^3$, $R^4$, $R^6$, $R^7$ and X are as defined immediately above and $R^5$ is bromo or chloro. In the same manner but treating the above described intermediate having an 2-ethoxy-2-oxoethyl group on the nitrogen of the bicyclic ring system with thionyl or chloride and hydrolyzing the resulting product under aqueous alkaline conditions, in the same manner as described above, gives the corresponding compound of formula I in which $R^1$, $R^3$, $R^4$, $R^6$, $R^7$ and X are as defined herein, $R^2$ is carboxymethyl and $R^5$ is bromo or chloro.

The following examples illustrate further this invention.

EXAMPLE 1

1,3-Dihydro-3-(2-ethyl-2-hydroxybutyl)-2H-isoindol-1-one (I: $R^1$, $R^2$, $R^6$ and $R^7$=H, $R^3$ and $R^4$=Et, $R^5$=OH and X=CO)

A solution of 2,3-dihydro-3-oxo-1H-isoindole-1-acetic acid (described by F. M. Rowe et al., cited above, 2.0 g) in ethanol (40 ml) containing p-toluene-sulfonic acid (0.10 g) is refluxed with stirring for 4.0 hr. Most of the ethanol is evaporated and the residue is dissolved in chloroform. The solution is washed with water, dried and evaporated. The residue (2.2 g) is crystallized from benzenehexane to give ethyl 1,3-dihydro-3-oxo-2H-isoindole-1-acetate, mp 116°–118° C.

A solution of the later compound (10.0 g, 0.045 mol) in 600 ml of tetrahydrofuran is added dropwise to a solution of ethyl magnesium iodide (prepared from 5.47 g of magnesium and 35.6 g of ethyl iodide in 200 ml of diethyl ether). The reaction is refluxed for 20 hr with stirring, cooled and poured into 500 ml of ice-cold 10% sulfuric acid. The solution is extracted with chloroform and the chloroform extract is washed with 5% aqueous sodium bicarbonate and water, dried and evaporated. The residue is chromatographed on silica gel using acetone-toluene (1:1) and the eluates are evaporated to give 7.0 of a residue. The residue is crystallized from ethyl acetate-diethyl ether to give the title compound (5.1 g): mp 130°–132° C. and Anal. Calcd for $C_{14}H_{19}NO_2$: C, 72.07% H, 8.21% N, 6.00% and Found: C, 72.07% H, 8.22% N, 5.95%.

In the same manner, but replacing ethyl magnesium iodide with an equivalent amount of propyl magnesium iodide, pentyl magnesium iodide or phenyl magnesium bromide, the following compounds of formula I are obtained respectively: 1,3-dihydro-3-(2-hydroxy-2-propylpentyl)-2H-isoindol-1-one, (I: $R^1$, $R^2$, $R^6$ and $R^7$=H, $R^3$ and $R^4$=Pr, $R^5$=OH and X=CO), mp 134°–135° C. (crystallized from ethyl acetate-petroleum ether); ir(CHCl$_3$) 3600, 3400 and 1685 cm$^{-1}$; nmr(CDCl$_3$) δ1.0 (t, 6H), 2.8 (s, 1H), 4.7 (m, 1H) and 7.4 (m, 4H); and Anal. Calcd for $C_{16}H_{23}NO_2$: C, 73.53% H, 8.87% N, 5.36% and Found: C, 73.20% H, 8.95% N, 5.12%; 1,3-dihydro-3-(2-hydroxy-2-pentylheptyl)-2H-isoindol-1-one, (I: $R^1$, $R^2$, $R^6$ and $R^7$=H,$R^3$ and $R^4$=pentyl, $R^5$=OH and X=CO), and 1,3-dihydro-3-(2-hydroxy-2,2-diphenylethyl)-2H-isoindol-1-one, (I: $R^1$, $R^2$, $R^6$ and $R^7$=H, $R^3$ and $R^4$=Ph, $R^5$=OH and X=CO), mp 232°–235° C. (crystallized from ethyl acetate-diethyl ether) and Anal. Calcd for $C_{22}H_{19}NO_2$: C, 80.22% H, 5.81% N, 4.25% and Found: C 79.86% H, 5.71% N, 4.14%.

EXAMPLE 2

1,3-Dihydro-3-(2-hydroxy-2-methylpropyl)-1-oxo-isoindole-2-acetic Acid (I: $R^1$, $R^6$ and $R^7$=H, $R^2$=CH$_2$COOH, $R^3$ and $R^4$=Me, $R^5$=OH and X=CO)

A solution of 2,3-dihydro-3-oxo-1H-isoindole-1-acetic acid (described by F. M. Rowe et al., cited above, 130 g, 0.682 mol) in methanol (1300 ml) containing 6.5 g of p-toluenesulfonic acid is refluxed with stirring for 3.5 hr. Most of the methanol is evaporated and the residue is dissolved in chloroform. The solution is washed with 5% aqueous sodium bicarbonate and water, dried and evaporated. The residue (125 g) is crystallized from isopropanol to give methyl 1,3-dihydro-3-oxo-2H-isoindole-1-acetate, mp 136°–138° C.

A solution of the latter compound (7.2 g, 0.035 mol) in 250 ml of tetrahydrofuran is added dropwise to a solution of methyl magnesium iodide (prepared from magnesium, 4.11 g, 0.075 gram-atoms and methyl iodide, 23.8 g, 0.168 mole, in 200 ml of diethyl ether). The reaction is refluxed for 18 hr with stirring, cooled and poured into 350 ml of ice-cold 10% sulfuric acid. The solution is extracted with chloroform and the chloroform extract is washed with 5% aqueous sodium bicarbonate and water, dried and evaporated. The residue is crystallized from benzene to give 1,3-dihydro-3-(2-hydroxy-2-methylpropyl)-2H-isoindol-1-one (4.8 g), mp 122°–123° C., Anal. Calcd for $C_{12}H_{15}NO_2$: C, 70.22% H, 7.37% N, 6.82% and Found: C, 70.11% H, 7.37% N, 6.96%.

A solution of the latter compound (8.0 g, 0.039 mol) in dimethylformamide (50 ml) is added to a stirring suspension of sodium hydride (1.87 g of a 50% dispersion in mineral oil, 0.39 mol) in dimethylformamide (40 ml). The mixture is stirred for 15 min at room temperature and a solution of ethyl bromoacetate (6.5 g, 0.047 mol) in dimethylformamide (15 ml) is added dropwise. After addition, the mixture is stirred at 40°–50° C. for 3 hr and poured into water. The mixture is extracted with ethyl acetate and the organic extract is washed with water, dried and evaporated to give an oily residue (9.8 g). This residue is chromatographed on silica gel using acetone-toluene (3:7) and the eluates are evaporated to give 7.0 g of 1,3-dihydro-3-(2-hydroxy-2-methylpropyl)-1-oxo-2H-isoindole-2-acetic acid ethyl ester, nmr(CDCl$_3$) δ 1.2 (t, 3H), 1.3 (3H), 1.4 (3H), 1.75 (s, 1H), 2.0 (d, 2H), 4.15 (q, 2H), 4.4 (m, 2H), 4.9 (m, 1H) and 7.5 (m, 4H).

A solution of the latter ester (7.0 g, 0.024 mol) in 165 ml of ethanol containing sodium hydroxide (3.28 g, 0.082 mol) in 10 ml of water is stirred at room temperature for 0.5 hr. The solution is cooled to ice-bath temperature, neutralized with a solution of hydrogen chloride in ethanol and evaporated. The residue is dissolved in water and the solution is acidified with 6 N hydrochloric acid. The precipitate is collected, dried and crystallized from isopropanol-water to give the title compound (4.85 g): mp 198°–199° C.; ir (CHCl$_3$) 3260, 2900, 1730 and 1675 cm$^{-1}$; nmr(DMSO-d$_6$) δ 1.2 (s, 3H), 1.25 (s, 3H), 1.9 (d, 2H), 4.15 and 4.45 (d, 2H), 4.75 (t, 1H) and 7.6 (m, 4H; and Anal. Calcd for $C_{14}H_{17}NO_4$: C, 63.86% H, 6.50% N, 5.32% and Found: C, 63.70% H, 6.72% N, 5.23%.

EXAMPLE 3

1,3-Dihydro-3-(2-hydroxy-2-methylpropyl)-5-methoxy-2H-isoindol-1-one (I: $R^1$=5-OMe, $R^2$, $R^6$ and $R^7$=H, $R^3$ and $R^4$=Me, $R^5$=OH and X=CO)

A solution of sodium nitrite (3.19 g) in water (23.6 ml) is slowly added to a stirring solution of 6-methoxy-2-naphthol [8.0 g, prepared as described in Organic Synthesis 49, 90 (1969)] in acetic acid (46 ml) and water (4.6 ml) at 0° C. The resulting slurry is allowed to stand at room temperature for several hours and diluted with water. The solid is collected, washed, dried and crystallized from methanol to give 6-methoxy-1nitroso-2-naphthol, mp 147°–148° C.

A solution of the latter compound (5.8 g) and p-toluenesulphonyl chloride (5.43 g) in acetone (100 ml) is kept at 55°–60° C. while 10% sodium hydroxide (50 ml) is added slowly, with constant shaking, so that the solution is kept faintly alkaline. When the solution finally becomes permanently alkaline, it is cooled, filtered and acidified. The oil is collected to obtain 5.5 g of 2-cyano-5-methoxycinnamic acid.

Similarly, by using 7-methoxy-1-nitroso-2-naphthol (described by L. F. Fieser and R. H. Brown, cited above), 2-cyano-4-methoxycinnamic acid is obtained.

A solution of 2-cyano-5-methoxycinnamic acid (5.5 g) in 10% sodium hydroxide (30 ml) is refluxed for 3 hr, cooled, acidified with hydrochloric acid and left overnight. The dark brown precipitate is collected, refluxed with diethyl ether (500 ml) and collected to obtain 4.5 g of 1,3-dihydro-5-methoxy-2H-1-oxo-isoindole-3-acetic acid: mp 192°–193° C. and nmr (DMSO-d$_6$) δ 2.6 (m, 2H), 3.8 (s, 3H), 4.7 (t, 1H), 7.25 (m, 3H) and 8.25 (s, 1H).

Similarly, by using 2-cyano-4-methoxycinnamic acid, the following compound is obtained, 1,3-dihydro-6-methoxy-2H-1-oxo-isoindole-3-acetic acid: mp 195°–197° C. (crystallized from methanol); ir (nujol) 3320, 2900, 1705, 1655 and 1230 cm$^{-1}$; uv max (MeOH) 293 nm ($\epsilon$=3250); nmr (CDCl$_3$) δ 2.6 (m, 2H), 4.75 (t, 1H), 7.3 (m, 3H), 8.5 (s, 1H) and 12.0 (s, 1H); and Anal. Calcd for C$_{11}$H$_{11}$NO$_4$: C, 59.72% H, 5.01% N, 6.33% and Found: C, 59.72% H, 5.06% N, 6.35%.

A solution of 1,3-dihydro-5-methoxy-2H-1-oxo-isoindole-3-acetic acid (4.5 g) and p-toluenesulfonic acid (20 mg) in dry methanol (40 ml) is refluxed for 4 hr and evaporated. The residue is chromatographed on silica gel using chloroform. The appropriate eluates are evaporated and crystallized from dichloromethane-diethyl ether to give 2.1 g of 1,3-dihydro-5-methoxy-2H-1-oxo-isoindole-3-acetic acid methyl ester: mp 133°–134° C.; ir (CHCl$_3$) 3440, 3200, 1730 and 1690 cm$^{-1}$; uv max (MeOH) 284 nm ($\epsilon$=13,492); nmr (CDCl$_3$) δ 2.7 (d, 2H), 3.75 (s, 3H), 3.85 (s, 3H), 4.85 (d, 1H) and 7.3 (m, 4H); and Anal Calcd for C$_{12}$H$_{13}$NO$_4$: C, 61.27% H, 5.57% N, 5.96% and Found: C, 61.23% H, 5.56% N, 6.04%.

Similarily, by using 1,3-dihydro-6-methoxy-2H-isoindole-3-acetic acid, the following ester is obtained, 1,3-dihydro-6-methoxy-2H-1-oxo-isoindole-3-acetic acid methyl ester: mp 127°–128.5° C. (crystallized from dichloromethanediethyl ether); ir (nujol) 3160, 3060, 1733, 1690, 1683, 1235 and 1180 cm$^{-1}$; uv max (MeOH) 293 nm ($\epsilon$=3199); and Anal. Calcd for C$_{12}$H$_{13}$NO$_4$: C, 61.27% H, 5.57% N, 5.96% and Found: C, 61.32% H, 5.74% N, 6.14%.

A solution of freshly prepared methyl magnesium iodide (prepared from methyl iodide (8 g) and magnesium (1.37 g)) in dry diethyl ether (170 ml) is added over a period of 20 min to a solution at 30° to 40° C. of 1,3-dihydro-5-methoxy-2H-1-oxo-isoindole-3-acetic acid methyl ester (2.0 g) in dry tetrahydrofuran (190 ml). After addition, the reaction mixture is refluxed for 3 hr, stirred at room temperature for 18 hr, acidified with 0.05 N sulfuric acid (40 ml) and extracted with chloroform. The organic extract is washed with water, aqueous sodium bicarbonate and brine, dried and evaporated. The residue is chromatographed on silica gel using acetone-benzene (15:85). The appropriate eluates are evaporated and crystallized from dichloromethane-hexane to give the title compound (1.1 g): mp 136°–137° C.; ir(CHCl$_3$) 3600, 3400, 1685, 1250 and 1140 cm$^{-1}$; uv max (MeOH) 284 ($\epsilon$=2,840), 272 ($\epsilon$=4,145) and 251 nm ($\epsilon$=13,745); nmr (CDCl$_3$) δ 1.45 (s, 3H), 1.50 (s, 3H), 1.85 (m, 2H), 3.7 (s, 1H), 3.9 (s, 3H), 4.7 (m, 1H), 7.25 (m, 3H) and 7.4 (s, 1H); and Anal. Calcd for C$_{13}$H$_{17}$NO$_3$: C, 66.36; H, 7.28% N, 5.95% and Found: C, 66.11% H, 7.31% N, 5.97%.

Similarly, by using 1,3-dihydro-6-methoxy-2H-1-oxo-isoindole-3-acetic acid methyl ester, the following compound of formula I is obtained: 1,3-dihydro-3-(2-hydroxy-2-methylpropyl)-6-methoxy-2H-isoindol-1-one (I: R$^1$=6-OMe, R$^2$, R$^6$ and R$^7$=H, R$^3$ and R$^4$=Me, R$^4$=OH and X=CO), mp 134°–136° C. (crystallized from dichloromethane-diethyl ether); ir (CHCl$_3$) 3500, 3300 and 1645 cm$^{-1}$; uv max (MeOH) 293 nm ($\epsilon$=3,360); nmr (CDCl$_3$) δ 1.4 (s, 3H), 1.5 (s, 3H), 1.8 (m, 2H), 3.6 (s, 1H), 3.85 (s, 3H), 4.7 (m, 1H), 7.2 (m, 3H) and 7.75 (s, 1H): and Anal. Calcd for C$_{13}$H$_{17}$NO$_3$: C, 66.36% H, 7.28% N, 5.95% and Found: C, 66.55% H, 7.21% N, 5.90%.

EXAMPLE 4

2-Bromo-6-methylbenzenamine

A mixture of mercuric acetate (100 g, 0.31 mol) and 4-nitrotoluene (500 g, 3.6 mol) is heated at 150° C. for 4 hr. A small amount of precipitate is filtered off and a saturated salt solution is added. The reaction is steam distilled to remove unreacted 4-nitrotoluene (about 350 ml). A gold colored precipitate is filtered off (100 g), crushed to a fine powder and added portionwise to bromine (50 g) in a cold saturated solution of potassium bromide (80 g). This is stirred for 1 hr and chloroform and water is added. A solid by-product is filtered off. The aqueous phase is extracted with chloroform. The combined chloroform extracts are dried and evaporated to afford 90 g of semisolid. Chromatography on silica gel using 80% acetone in toluene gives 46 g of 3-bromo-2-nitrotoluene: nmr (CDCl$_3$) δ 2.5 (s, 3H) and 7.8 (m, 3H).

A solution of stannous chloride (142 g) in 150 ml of concentrated hydrochloric acid is added portionwise to 3-bromo-2-nitrotoluene (46 g, 0.21 mol) while heating and swirling on the steam bath. After the addition is complete, the reaction is heated for 1.5 hr, the distillate is saturated with sodium chloride and extracted with chloroform. The combined chloroform extracts are dried and evaporated to give 39 g of oil. Chromatography on silica gel with 8% acetone in toluene affords 28 g of the title compound: nmr (CDCl$_3$) δ 2.1 (s, 3H), 3.6 (s, 2H) and 7.10 (m, 3H). The title compound is described by H. Burton et al., J. Chem. Soc., 1802 (1926).

Solid 2-nitro-3-methylanisole (20 g) is added portion to a hot (40°-60° C.) suspension of iron (30 g) in 20% acetic acid (400 ml). The mixture is heated on a steam bath for 40 min, filtered still hot and neutralized (after cooling) with 50% aqueous sodium hydroxide. The mixture is steam distilled (2 liters of water collected). The distillate is extracted with diethyl ether and the etheral solution is dried and evaporated to give an oily residue of 2-methoxy-6-methylbenzenamine: nmr (CDCl$_3$) δ2.15 (s, 3H), 3.7 (s, 2H), 3.8 (s, 3H) and 6.7 (m, 3H).

EXAMPLE 5

2-Chloro-6-methylbenzonitrile (II: R$^1$=2-Cl and Y=CN)

Sodium cyanide (65 g, 1.33 mol) in 100 ml of water is added to cuprous chloride (49.5 g, 0.5 mol) in 200 ml of water while stirring mechanically in a 5 l. 3-necked flask. Evolution of heat resulted and the cuprous chloride dissolves. This is then cooled in an ice bath to 0° C. A milky suspension of cuprous cyanide results. To this is added 100 ml of toluene. 6 N Hydrochloric acid (140 ml) is added slowly to 6-chloro-2-methylbenzenamine (56 g, 0.4 mol) while swirling in a 2 l. erlenmeyer flask and keeping the temperature at 0° C. A solution of sodium nitrite (28 g, 0.4 mol) in 80 ml of water is added dropwise to the hydrochloride suspension. Ice is added, when required, keeping the temperature at 0° C. Anhydrous sodium carbonate is added until the diazonium hydrochloride solution is neutral to pH paper. This is then added slowly to the cold stirring cuprous cyanide suspension, the temperature not being allowed to rise above 5° C. The reaction is then stirred at 0°–5° C. for 0.75 hr, allowed to reach room temperature over a 3 hr period and then heated on the steam bath at 50° C. After remaining at room temperature overnight, the product is steam distilled off. The distillate (3.5 l.) is extracted with benzene, dried and evaporated to give 2.8 g of the title compound, nmr (CDCl$_3$) δ 2.55 (s, 3H) and 7.3 (m, 3H).

In the same manner but replacing 6-chloro-2-methylbenzenamine with an equivalent amount of 2-bromo-6-methylbenzenamine (described in Example 4), 2-methoxy-6-methylbenzenamine (described in Example 4), 5-chloro-2-methylbenzenamine, 4-chloro-2-methylbenzenamine or 5-fluoro-2-methylbenzenamine: the following compounds of formula II are obtained respectively: 2-bromo-6-methylbenzonitrile, mp 44°–45° C.; 2-methoxy-6-methylbenzonitrile, mp 60°–62° C.; 5-chloro-2-methylbenzonitrile, mp 43°–45° C. (crystallized from petroleum etherhexane); 4-chloro-2-methylbenzonitrile; and 5-fluoro-2-methylbenzonitrile, mp 43°–45° C.

EXAMPLE 6

2-Chloro-6-(α,α-dibromomethyl)-benzonitrile (III: $R^1$=2-Cl and Y=CN)

A refluxing and stirring mixture of 2-chloro-6-methylbenzonitrile (31.6 g, 0.21 mol, described in Example 5) and N-bromosuccinimide (85.3 g, 0.5 mol) in 600 ml of carbon tetrachloride is irradiated with a 500 W photospot lamp for 8 hr. The reaction is cooled, filtered and the filtrate is evaporated. Chromatography on silica gel with 50% benzene in hexane gives 32 g of a residue. This residue is crystallized from benzene-hexane to give the title compound: mp 120°–122° C.; nmr (CDCl$_3$) δ 6.95 (s, 1H) and 7.6 (m, 3H); Anal. Calcd for C$_8$H$_4$Br$_2$ClN: C, 31.05% H, 1.30% N, 4.52% and Found: C, 31.35% H, 1.34% N, 4.59% and ir (CHCl$_3$) 2225 cm$^{-1}$.

In the same manner but replacing 2-chloro-6-methylbenzonitrile with another compound of formula II described in Example 5, the following compounds of formula III are obtained respectively: 2-bromo-6-(α,α-dibromomethyl)-benzonitrile, mp 78°–79° C. (crystallized from diethyl ether-petroleum ether), nmr (CDCl$_3$) δ 6.85 (s, 1H) and 7.75 (m, 3H) and Anal. Calcd for C$_8$H$_4$Br$_3$N: C, 27.15% H, 1.14% N, 3.95% and Found: C, 27.31% H, 1.17% N, 3.97%; 6-(α,α-dibromomethyl)-2--methoxybenzonitrile, mp 135°–136° C. (crystallized from dichloromethane-diethyl ether); 5-chloro-2-(α,α-dibromomethyl)-benzonitrile, mp 70°–73° C. nmr (CDCl$_3$) δ 6.9 (s, 1H) and 7.8 (m, 3H) and Anal. Calcd for C$_8$H$_4$ClBr$_2$N: C, 31.05% H, 1.30% N, 4.53% and Found: C, 31.55% H, 1.32% N, 4.57%; 4-chloro-2-(α,α-dibromomethyl)-benzonitrile, mp 116°–118° C. (crystallized from hexane-toluene), nmr (CDCl$_3$) δ 6.9 (s, 1H), 7.45 (m, 2H) and 8.0 (m, 1H) and Anal. Calcd for C$_8$H$_4$Br$_2$ClN: C, 31.05% H, 1.30% N, 4.53% and Found: C, 31.68% H, 1.35% N, 4.67%; and 5-fluoro-2-(α,α-dibromomethyl)-benzonitrile, nmr (CDCl$_3$) δ 6.9 (s, 1H) and 7.7 (m, 3H).

EXAMPLE 7

3-Chloro-2-cyanobenzaldehyde (IV: $R^1$=2-Cl and Y=CN)

Silver nitrate (57.1 g, 0.336 mol) in 955 ml of 95% ethanol is added dropwise to a solution of 2-chloro-6-(α,α-dibromomethyl)-benzonitrile (51.9 g, 0.168 mol) in 600 ml of 95% ethanol at 60° C. This is stirred for 0.75 hr, more silver nitrate solution (5.7 g in 95 ml of 95% ethanol) is added and stirring continued for a further 2 hr. Saturated sodium chloride solution (60 ml) is added and the reaction is filtered. The filter cake is washed with diethyl ether and the filtrate is evaporated to dryness. The residue is taken into diethyl ether, washed and dried to give 31 g of solid. Chromatography on silica gel using 20% hexane in benzene gives 21.5 g of a residue. This residue is crystallized from acetone-petroleum ether to give the title compound: mp 138°–140° C.; ir (CHCl$_3$) 2225 and 1703 cm$^{-1}$; nmr (CDCl$_3$) δ 8.0 (m, 3H) and 10.0 (s, 1H); and Anal. Calcd for C$_8$H$_{14}$ClNO: C, 58.02% H, 2.41% N, 8.46% and Found: C, 58.35% H, 2.44% N, 8.76%.

In the same manner, but replacing 2-chloro-6-(α,α-dibromomethyl)-benzonitrile with another compound of formula III described in Example 6, the following compounds of formula IV are obtained respectively: 3-bromo-2-cyanobenzaldehyde, mp 127°–130° C. (crystallized from ethyl acetate-petroleum ether), ir (CHCl$_3$) 2220 and 1695 cm$^{-1}$ and nmr (CDCl$_3$) δ 7.75 (m, 3H) and 10.25 (s, 1H); 2-cyano-3-methoxybenzaldehyde, mp 125°–126° C. (crystallized from benzene) and nmr (CDCl$_3$) δ 4.0 (s, 3H), 7.5 (m, 3H) and 10.2 (s, 1H); 4-chloro-2-cyanobenzaldehyde, mp 133°–135° C. (crystallized from acetone-petroleum ether), nmr (CDCl$_3$) δ 7.8 (m, 3H) and 10.2 (s, 1H) and Anal. Calcd for C$_8$H$_4$ClNO: C, 58.03% H, 2.44% N, 8.46% and Found: C, 57.80% H, 2.39% N, 8.69%; 5-chloro-2-cyano-benzaldehyde mp 113°–115° C. (crystallized from hexane-toluene), nmr (CDCl$_3$) δ 7.8 (m, 3H) and 10.25 (s, 1H) and Anal. Calcd for C$_8$H$_4$ClNO: C, 58.03% H, 2.44% N, 8.46% and Found: C, 58.13% H, 2.69% N, 8.65%; and 2-cyano-4-fluorobenzaldehyde, mp 115°–117° C. (crystallized from diethyl ether-hexane), nmr (CDCl$_3$) δ 7.4 (m, 2H), 8.05 (m, 1H) and 10.25 (s, 1H) and Anal. Calcd for C$_8$H$_4$FNO: C, 64.43% H, 2.70% N, 9.39% and Found: C, 64.13% H, 2.59% N, 9.34%.

EXAMPLE 8

3-(3-Chloro-2-cyanophenyl)-2-propenoic Acid (VI: $R^1$=3-Cl and Y=CN)

A mixture consisting of 3-chloro-2-cyanobenzaldehyde (20.5 g, 0.124 mol), malonic acid (24.4 g, 0.234 mol), pyridine (263 ml) and piperidine (2.6 ml) is stirred for 0.5 hr at 80° C., then at 100° C. for 1 hr, and then at reflux for 0.5 hr. After cooling it is poured into 1000 ml of 3 N hydrochloric acid in a beaker. This is stirred for 10 min and the resulting precipitate is filtered off to give 24.4 g of a dark-brown solid of the title compound.

In the same manner but replacing 3-chloro-2-cyanobenzaldehyde with an equivalent amount of another compound of formula IV described in Example 7, the following compounds of formula VI are obtained respectively: 3-(3-bromo-2-cyanophenyl)-2-propenoic acid, mp 130° C. (dec); 3-(2-cyano-3-methoxyphenyl)-2-propenoic acid; 3-(4-cyanophenyl)-2-propenoic acid, mp 267°-270° C. and Anal. Calcd for $C_{10}H_6ClNO_2$: C, 57.85% H, 2.91% N, 6.75% and Found: C, 57.83% H, 2.94% N, 6.59%; 3-(5-chloro-2-cyanophenyl)-2-propenoic acid, mp 174°-176° C. (crystallized from isopropanol-cyclohexane) and nmr ($CDCl_3$) δ 6.85 (d, 1H); and 7.8 (m, 4H); and 3-(2-cyano-4-fluorophenyl)-2-propenoic acid.

EXAMPLE 9

4-Chloro-2,3-dihydro-3-oxo-1H-isoindole-1-acetic Acid (VII: $R^1$=4-Cl, $R^2$, $R^6$ and $R^8$=H and X=CO)

3-(3-Chloro-2-cyanophenyl)-2-propenoic acid (24.4 g, 0.18 mol, described in Example 8) is refluxed with stirring in 150 ml of 10% sodium hydroxide solution for 3 hr. After cooling, and acidifying with 12 N hydrochloric acid, the reaction is allowed to stand at 4° C. for 18 hr. The resulting precipitate is filtered, washed with a little water and dried to afford 8.1 g of a solid. This solid is crystallized from water to give the title compound; mp 194°-198° C.; ir (nujol) 3250, 1700 and 1650 cm$^{-1}$; nmr (DMSO-$d_6$) δ 2.7 (m, 2H), 4.8 (t, 1H), 7.5 (m, 3H), 8.6 (s, 1H) and 12.3 (s, 1H); and Anal. Calcd for $C_{10}H_8ClNO_3$: C, 53.22% H, 3.57% N, 6.21% and Found: C, 53.11% H, 3.50% N, 6.35%.

In the same manner, but replacing 3-(3-chloro-2-cyanophenyl)-2-propenoic acid with another compound of formula VI described in Example 8, the following compounds of formula VII are obtained respectively: 4-bromo-2,3-dihydro-3-oxo-1H-isoindole-1-acetic acid; 4-methoxy-2,3-dihydro-3-oxo-1H-isoindole-1-acetic acid; 5-chloro-2,3-dihydro-3-oxo-1H-isoindole-1-acetic acid, mp 181°-183° C. (crystallized from water) and nmr (DMSO-$d_6$) δ 2.7 (m, 2H), 4.85 (t, 1H), 7.65 (m, 3H), 8.7 (s, 1H) and 12.4 (s, 1H); 6-chloro-2,3-dihydro-3-oxo-1H-isoindole-1-acetic acid, mp 175°-177° C. (crystallized from ethyl acetate), ir(nujol) 3400, 3260, 1705 and 1640 cm$^{-1}$ and nmr (DMSO-$d_6$) δ 2.75 (m, 2H), 4.9 (t, 1H), 7.1 (m, 3H), 8.65 (s, 1H) and 12.4 (s, 1H); and 5-fluoro-2,3-dihydro-3-oxo-1H-isoindole-1-acetic acid, mp <260° C.

EXAMPLE 10

4-Chloro-2,3-dihydro-3-oxo-1H-isoindole-1-acetic Acid Ethyl Ester (VII: $R^1$=4-Cl, $R^2$ and $R^6$=H, $R^8$=Et and X=CO)

4-Chloro-2,3-dihydro-3-oxo-1H-isoindole-1-acetic acid (8.1 g, 0.0279 mol, described in Example 9) in 170 ml of absolute ethanol containing 0.34 g of p-toluenesulfonic acid is refluxed and stirred for 5 hr. The reaction is cooled, the ethanol is evaporated off, and the residue is taken into chloroform. The solution is washed twice with 5% aqueous sodium bicarbonate and once with water, dried and evaporated to give 6.3 g of 4-chloro-2,3-dihydro-3-oxo-1H-isoindole-3-acetic acid, ethyl ester.

Similarily, by using 4-methoxy-2,3-dihydro-3-oxo-1H-isoindole-1-acetic and methanol in the presence of thionyl chloride, the following compound of formula VII is obtained, 4-methoxy-2,3-dihydro-3-oxo-1H-isoindole-1-acetic acid methyl ester: mp 121°-122° C. (crystallized from diethyl ether), nmr ($CDCl_3$) δ2.7 (2d, 2H), 3.75 (s, 3H), 3.95 (s, 3H), 4.8 (2d, 1H), 6.75 (s, 1H) and 7.1 (m, 3H) and Anal. Calcd for $C_{12}H_{13}NO_4$: C, 61.27% H, 5.57% N, 5.96% and Found: C, 61.49% H, 5.56% N, 5.90%.

In the same manner, but replacing 4-chloro-2,3-dihydro-3-oxo-1H-isoindole-3-acetic acid with another compound of formula VII described in Example 9, the following compounds of formula VII are obtained respectively: 4-bromo-2,3-dihydro-3-oxo-1H-isoindole-1-acetic acid ethyl ester, mp 157°-158° C. (crystallized from isopropanol-petroleum ether), nmr ($CDCl_3$) δ 1.3 (t, 3H), 2.7 (d, 2H), 4.2 (q, 2H), 4.85 (2d, 1H), 6.9 (s, 1H) and 7.6 (m, 3H) and Anal. Calcd for $C_{12}H_{12}BrNO_3$: C, 48.34% H, 4.06% N, 4.70% and Found: C, 48.12% H, 3.99% N, 4.51%; 5-chloro-2,3-dihydro-3-oxo-1H-isoindole-1-acetic acid ethyl ester, mp 163°-165° C. (crystallized from ethyl acetate-diethyl ether), nmr ($CDCl_3$) δ 1.3 (t, 3H), 2.75 (2d, 2H), 4.2 (q, 2H), 4.9 (2d, 1H), 7.1 (s, 1H) and 7.5 (m, 3H) and Anal. Calcd for $C_{12}H_{12}ClNO_3$: C, 56.81% H, 4.77% N, 5.52% and Found: C, 56.84% H, 4.88% N, 5.53%; 6-chloro-2,3-dihydro-3-oxo-1H-isoindole-1-acetic acid ethyl ester, mp 153°-155° C. (crystallized from diethyl ether), nmr ($CDCl_3$) δ 1.3 (t, 3H), 2.3-3.1 (m, 2H), 4.2 (q, 2H), 4.9 (2d, 1H), 7.1 (s, 1H) and 7.5 (m, 3H) and Anal. Calcd for $C_{12}H_{12}ClNO_3$: C, 56.81% H, 4.77% N, 5.52% and Found: C, 55.61% H, 4.79% N, 5.23%; and 5-fluoro-2,3-dihydro-3-oxo-1H-isoindole-1-acetic acid ethyl ester, mp 125°-128° C. (crystallized from diethyl ether), nmr ($CDCl_3$) δ 1.3 (t, 3H), 2.7 (2d, 2H), 4.2 (q, 2H), 4.9 (2d, 1H), 7.0 (s, 1H) and 7.3 (m, 3H) and Anal. Calcd for $C_{12}H_{12}FNO_3$: C, 60.75% H, 5.10% N, 5.90% and Found: C, 60.76% H, 5.08% N, 5.65%.

EXAMPLE 11

7-Chloro-1,3-dihydro-3-(2-hydroxy-2-methylpropyl)-2H-isoindol-1-one (I: $R^1$=7-Cl, $R^2$, $R^6$ and $R^7$=H, $R^3$ and $R^4$=Me, $R^5$=OH and X=CO)

4-Chloro-2,3-dihydro-3-oxo-1H-isoindole-1-acetic acid ethyl ester (11.2 g, 0.0409 mol, described in Example 10) in 500 ml of dry tetrahydrofuran is added dropwise to a stirring solution of methyl magnesium iodide (prepared from 5.3 g of magnesium and 31.2 g of methyl iodide in 200 ml of dry diethyl ether) at reflux. The reaction is stirred at reflux for 3 hr, poured into 400 ml of 10% sulfuric acid-ice mixture and extracted with chloroform. The combined extracts are washed with 5% sodium bicarbonate and water, dried and evaporated to afford 11.0 g of a semisolid. Chromatography on silica gel using 50% acetone in benzene gives 8.2 g of pure title compound as a solid. This solid is crystallized from benzene: mp 154°-156° C., ir ($CHCl_3$) 3600, 3400 and 1695 cm$^{-1}$; nmr ($CDCl_3$) δ 1.35 (s, 3H), 1.47 (s, 3H), 1.8 (m, 2H), 3.1 (s, 1H), 4.67 (1H), 7.35 (m, 3H) and 7.45 (1H); and Anal. Calcd for $C_{12}H_{14}ClNO_2$: C, 60.13% H, 5.89% N, 5.84% and Found: C, 60.09% H, 5.82% N, 5.71%.

In the same manner, but replacing 4-chloro-2,3-dihydro-3-oxo-1H-isoindole-1-acetic acid ethyl ester with another compound of formula VII described in Example 10, the following compounds of formula I are obtained respectively: 1,3-dihydro-3-(2-hydroxy-2-methylpropyl)-7-methoxy-2H-isoindol-1-one (I: $R^1$=7-OMe, $R^2$, $R^6$ and $R^7$=H, $R^3$ and $R^4$=Me, $R^5$=OH and X=CO), mp 154°-155° C. (crystallized from dichloromethane-diethyl ether), ir ($CHCl_3$) 3,600, 3,400, 3,300, 1,685, 1,270 and 1,090 cm$^{-1}$, uv max (MeOH) 293 (ε =5,450) and 234 nm (ε=9,750), nmr ($CDCl_3$) δ 1.35 (s, 3H), 1.45 (s, 3H), 1.75 (m, 2H), 3.3 (s, 1H), 3.95 (s, 3H), 7.28% N, 5.95% and Found: C, 66.28% H, 7.41% N, 5.89%; 7-bromo-1,3-dihydro-3-(2-hydroxy-2- methylpropyl)-2H-isoindol-1-one (I: $R^1$=7-Br, $R^2$, $R^6$ and $R^7$=H, $R^3$ and $R^4$=Me, $R^5$=OH and X=CO), mp 151°–153° C. (crystallized from ethyl acetate-diethyl ether), ir (CHCl$_3$), 3,600, 3,400 and 1,695 cm$^{-1}$, nmr (CDCl$_3$) δ 1.57 (s, 3H), 4.7 (m, 1H), 7.5 (s, 1H) and 7.6 (m, 3H) and Anal. Calcd for $C_{12}H_{14}BrNO_2$: C, 50.72% H, 4.97% N, 4.93% and Found: C, 51.65% H, 4.97% N, 4.86%; 6-chloro-1,3-dihydro-3-(2-hydroxy-2-methylpropyl)-2H-isoindol-1-one (I: $R^1$=6-Cl, $R^2$, $R^6$ and $R^7$=H, $R^3$ and $R^4$=Me, $R^5$=OH and X=CO), mp 159°–161° C. (crystallized from ethyl acetate-petroleum ether), ir (CHCl$_3$) 3,590, 3,390 and 1,690 cm$^{-1}$, nmr (CDCl$_3$) δ 1.4 (s, 3H), 1.5 (s, 3H), 2.0 (m, 2H), 3.7 (s, 1H), 4.75 (s, 1H), 7.4 (m, 3H) and 7.65 (s, 1H) and Anal. Calcd for $C_{12}H_{14}ClNO_2$: C, 60.13% H, 5.89% N, 5.84% and Found: C, 60.14% H, 6.05% N, 6.01%; 5-chloro-1,3-dihydro-3-(2-hydroxy-2-methylpropyl)-2H-isoindol-1-one (I: $R^1$=5-Cl, $R^2$, $R^6$ and $R^7$=H, $R^3$ and $R^4$=Me, $R^5$=OH and X=CO), mp 144°–146° C. (crystallized from ethyl acetate-petroleum ether), ir (CHCl$_3$) 3,600, 3,400 and 1,685 cm$^{-1}$, nmr (CDCl$_3$) δ 1.4 (s, 3H), 1.5 (s, 3H), 1.9 (m, 2H), 3.3 (s, 1H), 4.75 (d, 1H) and 7.2–7.8 (m, 4H) and Anal. Calcd for $C_{12}H_{14}ClNO_2$: C, 60.13% H, 5.89% N, 5.84% and Found: C, 59.88% H, 5.71% N, 5.70% and 6-fluoro-1,3-dihydro-3-(2-hydroxy-2-methylpropyl)-2H-isoindol-1-one (I: $R^1$=6-F, $R^2$, $R^6$ and $R^7$=H, $R^3$ and $R^4$=Me, $R^5$=OH and X=CO), mp 135°–137° C. (crystallized from diethyl ether-hexane), ir (CHCl$_3$) 3,600, 3,400 and 1,695 cm$^{-1}$, nmr (CDCl$_3$) δ 1.4 (s, 3H), 1.5 (s, 3H), 1.85 (m, 2H), 3.1 (s, 1H), 4.7 (d, 1H), 7.25 (m, 3H) and 7.5 (s, 1H) and Anal. Calcd for $C_{12}H_{14}FNO_2$: C, 64.56% H, 6.32% N, 6.28% and Found: C, 64.98% H, 6.36% N, 6.01%.

EXAMPLE 12

2-(1-Methylethyl)-3-hydroxy-1,3-dihydro-2H-isoindol-1-one (XIV: $R^1$ is hydrogen and $R^2$ is 1-methylethyl)

A mixture of 1-isobenzofuranone (150 g) and N-bromosuccinimide (199.05 g) in carbon tetrachloride (3000 ml) is irradiated with a 500 W photospot lamp for 3 hr, cooled and filtered. The filtrate is evaporated to give 3-bromo-1-isobenzofuranone (240 g).

A solution of the latter compound (9.0 g) and isopropylamine (9 ml) in methanol (100 ml) is stirred at room temperature for 20 min and evaporated. The residue is chromatographed on silica gel using acetone-toluene (1:4) to give 7.4 g of the title compound, nmr (DMSO-d$_6$) δ 1.3 (d, 6H), 4.15 (m, 1H), 5.85 (d, 1H), 6.35 (d, 1H) and 7.5 (m, H).

Similarly, by replacing isopropyl amine with an equivalent amount of ethyl amine, the following compound of formula XIV is obtained, 2-ethyl-3-hydroxy-1,3-dihydro-2H-isoindol-1-one: mp 106°–108° C. (crystallized from benzene); ir (nujol) 3260 and 1675 cm$^{-1}$; nmr (DMSO-d$_6$) δ 1.15 (t, 3H), 3.5 (m, 2H), 5.8 (d, 1H), 6.5 (d, 1H) and 7.55 (m, 4H).

EXAMPLE 13

1,3-Dihydro-2-(1-methylethyl)-3-(2-oxopropyl)-2H-isoindol-1-one (X: $R^1$ and $R^6$=H, $R^2$=1-methylethyl, $R^4$=Me and X=CO)

A solution of 2-(1-methylethyl)-3-hydroxy-1,3-dihydro-2H-isoindol-1-one (6.1 g, described in Example 12) and ethyl acetoacetate (12.4 g) in conc. sulfuric acid (60 ml) is stirred at 40° C. for 24 hr and poured into ice. The solution is extracted with ethyl acetate and the organic extract is washed with 5% aqueous sodium bicarbonate and water, dried and evaporated. The residue is chromatographed on silica gel using hexane-ethyl acetate (2:3) and the eluates are evaporated to give 3.7 g of the title compound, nmr (DMSO-d$_6$) δ 1.25 (d, 3H), 1.35 (d, 3H), 2.05 (s, 3H), 2.5–3.4 (m, 2H), 3.95 (m, 1H), 4.9 (m, 1H) and 7.4 (m, 4H).

Similarily by using 2-ethyl-3-hydroxy-1,3-dihydro-2H-isoindol-1-one (described in Example 12), the following compound of formula X is obtained. 2-ethyl-1,3-dihydro-3-(2-oxopropyl)-2H-isoindol-1-one, nmr (DMSO-d$_6$) δ 1.1 (t, 3H), 2.1 (s, 3H), 2.7–3.85 (m, 4H), 4.95 (t, 1H) and 7.5 (m, 4H).

EXAMPLE 14

1,3-Dihydro-2-(1-methylethyl)-3-(2-hydroxy-2-methylpropyl)-2H-isoindol-1-one (I: $R^1$, $R^6$ and $R^7$=H, $R^2$=1-methylethyl, $R^3$ and $R^4$=Me, $R^5$=OH and X=CO)

A solution of 1,3-dihydro-2-(1-methylethyl)-3-(2-oxopropyl)-2H-isoindol-1-one (3.7 g, described in Example 13) in 80 ml of dry tetrahydrofuran (distilled over lithium aluminium hydride) is added dropwise to a stirred, refluxing solution of methyl magnesium iodide (prepared from 1.56 g of magnesium turnings and 9.08 g of methyl iodide in 30 ml of diethyl ether). The mixture is refluxed for 3 hr, poured into 10% sulfuric acid-ice mixture, and then extracted with ethyl acetate. The combined extracts are washed with 5% sodium bicarbonate and brine, dried and evaporated to give 4.1 g of semisolid. Chromatography on silica gel using 40% hexane in toluene followed by recrystallization from toluene-petroleum ether afforded 3.7 g of the title compound: mp 82°–84° C.; ir (CHCl$_3$) 3,600, 3,400 and 1,670 cm$^{-1}$, nmr (CDCl$_3$) δ 1.4 (m, 12H), 1.8 (s, 1H), 2.0 (m, 2H), 3.95 (m, 1H), 4.65 (m, 1H) and 7.5 (m, 4H); and Anal. Calcd for $C_{15}H_{21}NO_2$: C, 72.84% H, 8.56% N, 5.66% and Found: C, 72.54% H, 8.71% N, 5.45%.

Similarily, by using 2-ethyl-1,3-dihydro-3-(2-oxopropyl)-2H-isoindol-1-one (described in Example 13), the following compound of formula I is obtained: 2-ethyl-1,3-dihydro-3-(2-hydroxy-2-methylpropyl)-2H-isoindol-1-one (I: $R^1$, $R^6$ and $R^7$=H, $R^2$=Et, $R^3$ and $R^4$=Me, $R^5$=OH and X=CO): mp 100°–103° C. (crystallized from diethyl ether); ir (CHCl$_3$) 3,600, 3,420 and 1,675 cm$^{-1}$; nmr (CDCl$_3$) δ 1.2 (t, 3H), 1.35 (s, 6H), 1.8 (s, 1H), 1.9 (m, 2H), 3.7 (m, 2H), 4.7 (t, 1H) and 7.45 (m, 4H); and Anal. Calcd for $C_{14}H_{19}NO_2$: C, 72.07% H, 8.21% N, 6.00% and Found: C, 72.03% H, 8.24% N, 5.85%.

EXAMPLE 15

3-Chloro-2-methylbenzonitrile (II: $R^1$=3-Cl and Y=CN)

Sodium cyanide (58 g, 1.18 mol) in 90 ml of water is added to cuprous chloride (44 g, 0.44 mol) in 180 ml of water while stirring mechanically in a 5 l. 3-necked flask. Evolution of heat results and the cuprous chloride dissolves. This is then cooled in an ice bath to 0° C. A milky suspension of cuprous cyanide results. To this is added 90 ml of toluene. 6 N Hydrochloric acid (125 ml) is added slowly to 3-chloro-2-methylaniline (50 g, 0.35 mol) in a 2 l. erlenmeyer flask, while cooling and swirling. A solution of sodium nitrite (25 g, 0.36 mol) in 70 ml of water is added dropwise to the hydrochloride suspension. Ice is added when required, keeping the temperature at 0° C. Anhydrous sodium carbonate is added until the diazonium hydrochloride solution is neutral to pH paper. This is then added slowly to the cold stirring cuprous cyanide suspension, the temperature not being allowed to rise above 5° C. The reaction is then stirred at 0°-5° C. for 0.5 hr, allowed to reach room temperature over a 2 hr period and then heated to 50° C. on the steam bath. After remaining at room temperature overnight, the product is steam distilled off. The distillate is extracted with benzene, washed with 10% hydrochloric acid, dried and evaporated to afford 28 g of the title compound that solidified on standing.

A mixture of 3-hydroxy-2-methylbenzonitrile [23.38 g described by S. Gabriel and A. Thieme, Ber., 52, 1079 (1919)] anhydrous potassium carbonate (26.7 g) and methyl iodide (16.43 ml) in acetone (255 ml) is refluxed for 4 hr, cooled and filtered. The filtrate is evaporated and dissolved in dichloromethane. The solution is washed with water, dried and evaporated. The residue is chromatographed on silica gel using dichloromethane-hexane(1:1) and the eluates are evaporated and crystallized from hexane to obtain 2-methyl-3-methoxybenzonitrile: (II: $R^1$=2-Me and Y=CN): mp 47°-48° C.; ir 2,220, 1,265 and 1,100 cm$^{-1}$; and nmr (CDCl$_3$) $\delta$2.42 (s, 3H), 3.85 (s, 3H) and 7.15 (m, 3H).

EXAMPLE 16

3-Chloro-2-($\alpha$-bromomethyl)benzonitrile (XI: $R^1$=3-Cl)

A refluxing mechanically stirred mixture of 3-chloro-2-methylbenzonitrile (34 g, 0.24 mol, described in Example 15) and N-bromosuccinimide (99 g, 0.56 mol) in 500 ml of carbon tetrachloride is irradiated with a 500 W photospot lamp for 3 hr. The reaction is cooled, filtered and the filtrate is evaporated. The residue is crystallized from hexane to give 37.5 g of the title compound: mp 69°-71° C.; and Anal. Calcd for C$_8$H$_5$BrClN: C, 41.68% H, 2.19% N, 6.08% and Found: C, 41.97% H, 2.18% N, 6.15%.

Similarily, by replacing 3-chloro-2-methylbenzonitrile with an equivalent amount of 2-methyl-3-methoxybenzonitrile (described in Example 15)or 2,6-dimethylbenzonitrile [described by R. R. Herr et al., J. Amer. Chem. Soc., 79, 4229 (1957)], the following compounds of formula XI are obtained respectively, 2-($\alpha$-bromomethyl)-3-methoxybenzonitrile: mp 96.5°-97° C. (crystallized from benzene-hexane) and Anal. Calcd for C$_9$H$_8$BrNO: C, 47.81% H, 3.57% N, 6.20% and Found: C, 47.94% H, 3.57% N, 6.44%; and 2-($\alpha$-bromomethyl)-6-methylbenzonitrile.

EXAMPLE 17

4-Chloro-1-isobenzofuranone (XII: $R^1$=4-Cl)

A stirring mixture of 3-chloro-2-($\alpha$-bromomethyl)-benzonitrile (27.7 g, 0.12 mol, described in Example 16) in 800 ml of 7% nitric acid is refluxed for 2 hr and extracted thrice with benzene. The combined organic extracts are washed with saturated sodium chloride solution, dried and evaporated to afford 23.5 g of gold solid. Chromatography on silica gel with 40% hexane in toluene gave 15.4 g of the title compound: mp 80°-82° C; nmr (CDCl$_3$) $\delta$ 5.13 (s, 2H) and 7.4 (m, 3H); and Anal. Calcd for C$_8$H$_5$ClO: C, 57.00% H, 2.99% and Found: C, 56.82% H, 2.99%.

Similarily, by replacing 3-chloro-2-($\alpha$-bromomethyl)-benzonitrile with an equivalent amount of another compound described in Example 16, the following compounds of formula XII are obtained respectively, 7-bromo-4-methoxy-1-isobenzofuranone: mp 201°-202° C. (crystallized from ethanol); nmr (CDCl$_3$) $\delta$ 3.9 (s, 3H), 5.25 (s, 2H), 9.25 (d, 1H) and 7.65 (d, 1H); and Anal. Calcd for C$_9$H$_7$BrO$_3$: C, 44.47% H, 2.90% and Found: 44.38% H, 2.83%; and 7-methyl-1-isobenzofuranone: mp 76°-81° C.; and nmr (CDCl$_3$) $\delta$ 2.67 (s, 3H), 5.20 (s, 2H), 7.20 (m, 2H) and 7.48 (2d, 1H).

EXAMPLE 18

3-Bromo-4-chloro-1-isobenzofuranone (XIII: $R^1$=4-Cl)

A stirring refluxing mixture of 4-chloro-1-isobenzofuranone (2.35 g, 0.014 mol, described in Example 17) and N-bromosuccinimide (2.6 g, 0.014 mol) in 80 ml of carbon tetrachloride is irradiated with a 500 W photospot lamp for 1.5 hr. The reaction is cooled and filtered. The filtrate is evaporated to give 3.95 g of semi-solid. Chromatography on silica gel using 40% hexane in toluene afforded 2.4 g of off-white solid title compound: mp 70°-72° C.; and nmr (CDCl$_3$) $\delta$ 2.3 (s, 1H) and 7.7 (m, 3H).

Similarily, by replacing 4-chloro-1-isobenzofuranone with another compound of formula XII described in Example 17, the following compounds of formula XIII are obtained respectively: 3,7-dibromo-4-methoxy-1-isobenzofuranone; mp 178°-179.5° C. (crystallized from dichloromethane-hexane); nmr (CDCl$_3$) $\delta$ 3.95 (s, 3H), 7.0 (d, 1H), 7.15 (s, 1H) and 8.15 (d, 1H); and Anal. Calcd for C$_9$H$_6$Br$_2$O$_3$: C, 33.57% H, 1.88% and Found: C, 33.61% H, 1.84%; and 3-bromo-7-methyl-1-isobenzofuranone.

EXAMPLE 19

4-Chloro-1,3-dihydro-3-hydroxy-2H-isoindol-1-one (XIV: $R^1$=4-Cl)

A mixture of 3-bromo-4-chloro-isobenzofuranone (8.0 g, 0.032 mol described in Example 18) in 300 ml of methanol containing 15 ml of aqueous ammonia is heated on the steam bath until all the starting material has dissolved. Evaporation gives a solid residue. This is taken up in 12% methanol in chloroform, the ammonium bromide filtered off and the filtrate is chromatographed on silica gel with this solvent system to afford 4.5 g of solid title compound which is crystallized from acetone-hexane; mp 179°-181° C.; nmr (DMSO-d$_6$) $\delta$ 5.9 (d, 1H), 6.4 (d, 1H), 7.55 (m, 3H) and 9.0 (s, 1H); and Anal. Calcd for C$_8$H$_6$ClNO$_2$: C, 52.33% H, 3.29% N, 7.63% and Found: C, 52.36% H, 3.42% N, 7.95%.

Similarily, by replacing 3-bromo-4-chloro-1-isobenzofuranone with an equivalent amount of another compound of formula XIII described in Example 18 or 3-bromo-1-isobenzofuranone (described in Example 12), the following compounds of formula XIV are obtained respectively: 7-bromo-1,3-dihydro-3-hydroxy-4-methoxy-2H-isoindol-1-one; nmr (DMSO-d$_6$) $\delta$ 3.85 (s, 3H), 5.75 (d, 1H), 6.15 (d, 1H), 7.1 (d, 1H), 7.55 (d, 1H) and 8.85 (1H); 1,3-dihydro-3-hydroxy-7-methyl-2H-isoindol-1-one; mp 217°-218° C. (crystallized from water); and 1,3-dihydro-3-hydroxy-2H-isoindol-1-one; mp 146°-147° C. and Anal. Calcd for C$_8$H$_7$NO$_2$: C, 64.42% H, 4.73% N, 9.39% and Found: C, 64.12% H, 4.73% N, 9.54% (A. Reissert, Chem. Ber., 46, 1488 (1913) cites mp 171°-172° C. for this compound).

EXAMPLE 20

4-Chloro-1,3-dihydro-3-(2-oxopropyl)-2H-isoindol-1-one (X: $R^1$=4-Cl, $R^2$ and $R^6$=H, $R^4$=Me and X=CO)

4-Chloro-1,3-dihydro-3-hydroxy-2H-isoindol-1-one (4.0 g, described in Example 19) is added portionwise to a stirring solution of ethyl acetoacetate (8.0 g, 0.061 mol) in 20 ml of concentrated sulfuric acid. This is stirred at room temperature for 60 hr, poured into ice-water and extracted with ethyl acetate. The combined extracts are washed with 5% aqueous sodium bicarbonate, saturated salt solution, dried and evaporated to give 5 g of solid. Chromatography on silica gel with 30% acetone in toluene gives 4.0 g of pure title compound which is crystallized from acetone-hexane: mp 159°–161° C.; and nmr (CDCl$_3$δ 2.25 (s, 3H), 3.1 (m, 2H), 4.95 (d, 1H), 6.95 (s, 1H) and 7.5 (m, 3H).

Similarily, by replacing 4-chloro-1,3-dihydro-3-hydroxy-2H-isoindol-1-one with another compound of formula XIV described in Example 19, the following compounds of formula X are obtained respectively: 7-bromo-1,3-dihydro-4-methoxy-3-(2-oxopropyl)-2H-isoindol-1-one; mp 198°–199° C. (crystallized from dichloromethane-hexane); nmr (CDCl$_3$) δ 2.17 (s, 3H), 2.28 (d, 1H), 3.55 (d, 1H), 3.85 (s, 3H), 4.77 (m, 1H), 6.75 (s, 1H), 6.85 (d, 1H) and 7.48 (d, 1H); and Anal. Calcd for $C_{12}H_{12}BrNO_3$: C, 48.34% H, 4.06% N, 4.70% and Found: C, 48.13% H, 4.07% N, 4.86%; and 1,3-dihydro-7-methyl-3-(2-oxopropyl)-2H-isoindol-1-one; mp 132°–133° C. (crystallized from dichloromethane-diethyl ether) and nmr (CDCl$_3$) δ 2.17 (s, 3H), 2.31 (d, 1H), 3.10 (2d, 1H), 2.65 (s, 3H), 4.80 (2d, 1H), 6.50 (s, 1H) and 7.15 (m, 3H).

In a similar manner, by condensing 1,3-dihydro-3-hydroxy-2H-isoindol-1-one (described in Example 19) with ethyl 2-methylacetoacetate, the following compounds are obtained, isomer A of 1,3-dihydro-3-(1-methyl-2-oxopropyl)-2H-isoindol-1-one; mp 173°–175° C. (crystallized from ethyl acetate-hexane); nmr (CDCl$_3$) δ 0.8 (d, 3H), 2.25 (s, 3H), 3.1 (q, 1H), 4.9 (d, 1H), 6.65 (s, 1H), 7.45 (m, 3H) and 7.8 (m, 1H); and Anal. Calcd for $C_{12}H_{13}NO_2$: C, 70.91% H, 6.45% N, 6.89% and Found: C, 70.98% H, 6.28% N, 6.99%; and isomer B of 1,3-dihydro-3-(1-methyl-2-oxopropyl)-2H-isoindol-1-one; mp 89°–92° C. (crystallized from diethyl ether); nmr (CDCl$_3$) δ1 1.17 (d, 3H), 2.18 (s, 3H), 2.8 (m, 1H), 4.9 (d, 1H), 7.0 (s, 1H), 7.45 (m, 3H) and 7.8 (m, 1H); and Anal. Calcd for $C_{12}H_{13}NO_2$: C, 70.91% H, 6.45% N, 6.89% and Found: C, 70.57% H, 6.35% N, 6.99%.

EXAMPLE 21

1,3-Dihydro-4-methoxy-3-(2-oxopropyl)-2H-isoindol-1-one (X: $R^1$=4-MeO, $R^2$ and $R^6$=H, $R^4$=Me and X=CO)

A mixture of 7-bromo-1,3-dihydro-4-methoxy-3-(2-oxopropyl)-2H-isoindol-1-one (5.0 g, described in Example 20) and potassium carbonate (2.5 g) in ethanol (100 ml) is hydrogenated in the presence of 5% palladium on carbon (2.5 g) at atmospheric pressure and room temperature until 1.1 equivalent of hydrogen is absorbed. The mixture is filtered and the filtrate is evaporated. A solution of the residue in chloroform is washed with water, dried and evaporated. The residue is crystallized from dichloromethane-diethyl ether to give the title compound (2.7g): mp 176.5°–177.5° C.; nmr (CDCl$_3$) δ 2.20 (s, 3H), 2.30 (2d, 2H), 3.57 (2d, 2H), 3.87 (s, 3H), 4.85 (2d, 1H), 6.70(s, 1H), 6.97 (t, 1H) and 7.37(d, 2H); and Anal. Calcd for $C_{12}H_{13}NO_3$: C, 65.74% H, 5.98% N, 6.39% and Found: C, 65.64% H, 6.09% N, 6.70%.

EXAMPLE 22

4-Chloro-1,3-dihydro-3-(2-hydroxy-2-methylpropyl)-2H-isoindol-1-one (I: $R^1$=4-Cl, $R^2$, $R^6$ and $R^7$=H, $R^3$ and $Rr^4$=Me, $R^5$=OH and X=CO)

A solution of 4-chloro-1,3-dihydro-3-(2-oxopropyl)-2H-isoindol-1-one (3.8 g, described in Example 20) in 50 ml of dry tetrahydrofuran is added to a refluxing stirring solution of methyl magnesium iodide (prepared from 1.24 g of magnesium and 7.24 g of methyl iodide in 50 ml of dry diethyl ether). The reaction is stirred at reflux for 1 hr, poured into 100 ml of 10% sulfuric acid and ice. This is extracted with chloroform and the combined organic extracts are washed with 5% sodium bicarbonate and saturated salt solution, dried, and evaporated to give 4.4 g of solid. This is treated with charcoal and recrystallized from acetone-hexane to afford 2.0 g of pure title compound: mp 161°–163° C; nmr (CDCl$_3$) δ 1.4 (s, 3H), 1.5 (s, 3H), 2.2 (m, 2H), 3.05 (s, 1H), 4.85 (d, 1H) and 7.45 (m, 3H); ir (CHCl$_3$) 3,600, 3,390 and 1,690 cm$^{-1}$; and Anal. Calcd for $C_{12}H_{14}ClNO_2$: C, 60.13% H, 5.89% N, 5.84% and Found: C, 59.87% H, 5.86% N, 6.05%.

Similarily, by replacing 4-chloro-1,3-dihydro-3-(2-oxopropyl)-2H-isoindol-1-one with an equivalent amount of another compound of formula X described in Examples 20 and 21, the following compounds of formula I are obtained respectively: 7-bromo-1,3-dihydro-3-(2-hydroxy-2-methylpropyl)-4-methoxy-2H-isoindol-1-one (I: $R^1$=7-Br and 4-OMe, $R^2$, $R^6$ and $R^7$=H, $R^3$ and $R^4$= Me, $R^5$=OH and X=CO); mp 178.5°–179° C. (crystallized from dichloromethane); ir (nujol) 3,370, 3,240, 1,689 and 1,672 cm$^{-1}$; uv max (MeOH) 300 (ε=4,180) and 240 nm (ε=10,770); and Anal. Calcd for $C_{13}H_{16}BrNO_3$: C, 49.69% H, 5.13% N, 4.46% and Found: C, 49.72% H, 5.18% N, 4.43%; 1,3-dihydro-3-(2-hydroxy-2-methylpropyl)-7-methyl-2H-isoindol-1-one (I: $R^1$=7-Me, $R^2$, $R^6$ and $R^7$=H, $R^3$ and $R^4$=Me, $R^5$=OH and X=CO); mp 135°–136° C. (crystallized from dichloromethane-diethyl ether); ir (CHCl$_3$) 3,600, 3,420 and 1,685 cm$^{-1}$, uv max (MeOH) 283 (ε=2,390), 275 (ε=2,240) and 229nm (ε=10,845); and Anal. Calcd for $C_{13}H_{17}NO_2$: C, 71.21% H, 7.81% N, 6.39% and Found: C, 70.85% H, 7.77% N, 6.41%; [3S[3α(S*, S*)]]-1,3-dihydro-3-(3-hydroxy-3-methyl-2-butyl)-2H-isoindol-1-one (I: $R^1$, $R^2$, and $R^7$=H, $R^3$, $R^4$ and $R^6$=Me, $R^5$=OH and X=CO); mp 148°–150° C. (crystallized from ethyl acetate-petroleum ether); ir (CHCl$_3$) 3,600, 3,400 and 1,685 cm$^{-1}$; nmr (CDCl$_3$) δ 0.5 (d, 3H), 1.35 (s, 3H), 1.52 (s, 3H), 1.95 (m, 1H), 3.1 (s, 1H), 5.0 (s, 1H), 7.05 (s, 1H), 7.4 (m, 3H) and 7.8(m, 1H); and Anal. Calcd for $C_{13}H_{17}NO_2$: C, 71.20% H, 7.82% N, 6.39% and Found: C, 71.15% H, 7.80% N, 6.36%; [3R[3α(R,R)]]-1,3-dihydro-3-(3-hydroxy-3-methyl-2-butyl)-2H-isoindol-1-one (I: $R^1$, $R^2$ and $R^7$=H, $R^3$, $R^4$ and $R^6$=Me, $R^5$=OH and X= CO); mp 145°–147° C. (crystallized from ethyl acetate-petroleum ether); ir (CHCl$_3$) 3,600, 3,370 and 1,685 cm$^{-1}$; nmr (CDCl$_3$) δ 1.1 (d, 3H), 1.35 (s, 3H), 1.4 (s, 3H), 1.75 (m, 1H), 3.8 (s, 1H), 4.6 (d, 1H), 7.4 (m, 1H) and 7.85 (s, 1H); and Anal. Calcd for $C_{13}H_{17}NO_2$: C, 71.20% H, 7.82% N, 6.39% and Found: C, 71.25% H, 7.83% N, 6.47%; 1,3-dihydro-3-(2-hydroxy-2-methylpropyl)-4-methoxy-2H-isoindol-1-one (I: $R^1$=4-OMe, $R^2$, $R^6$ and $R^7$=H, $R^3$ and $R^4$=Me, $R^5$=OH and X=CO); mp 133°–135° C. (crystallized from dichloromethane-diethyl ether); ir (CHCl$_3$) 3,604, 3,360, 3,400, 2,840, 1,670 and 1,267 cm$^{-1}$; uv max (MeOH) 291 ($\epsilon$=3,200) and 286 nm ($\epsilon$=3,240); nmr (CDCl$_3$) δ 1.36 (x, 3H), 1.47(s, 3H), 1.75 (d, 1H), 2.41 (d, 1H), 3.08 (s, 1H), 4.75 (2d, 1H), 6.90 (m, 1H) and 7.35 (m, 2H); and Anal. Calcd for C$_{13}$H$_{17}$NO$_3$: C, 66.36% H, 7.28% N, 5.95% and Found: C, 66.06% H, 7.33% N, 5.84%.

EXAMPLE 23

2,3-Dihydro-α,α-dimethyl-1,2-benzisothiazole-3-ethanol (I: $R^1$, $R^2$, $R^6$ and $R^7$=H, $R^3$ and $R^4$=Me, $R^5$=OH and X=SO$_2$)

A solution of 1,1-benzisothiazoline-3-acetic acid, 1,1'-dioxide ethyl ester (2.0 g, described by B. K. Rao and G. H. Hamor, J. Pharm. Sci., 58, 628 (1969)] in 50 ml of dry tetrahydrofuran (distilled over lithium aluminum hydride) is added to a refluxing stirring solution of methyl magnesium iodide (prepared from 0.96 g of magnesium turnings, and 6.0 g of methyl iodide in 50 ml of dry diethyl ether). The reaction is stirred at reflux for 16 hr and poured into 60 ml of 10% sulfuric acid and ice. This is extracted with chloroform and the combined organic extracts are washed with 5% sodium bicarbonate and saturated salt solution, dried, and evaporated to give 2.5 g of brown oil. Chromatography on silica gel using 20% acetone in toluene affords 1.1 g solid title compound. Recrystallization is from ethyl acetate-diethyl ether; mp 130°–105° C.; ir (CHCl$_3$) 3,590, 3,480, 3,250, 1,295 and 1,155 cm$^{-1}$; nmr (CDCl$_3$) δ 1.35 (s, 3H), 1,44 (s, 3H), 1.80 (d, 1H), 2.10 (d, 1H), 1.95 (s, 1H), 4.90 (m, 1H), 6.25 (s, 1H) and 7.1–7.9 (m, 4H); and Anal. Calcd for C$_{11}$H$_{15}$NO$_3$S: C, 54.75% H, 6.27% N, 5.81% and Found: C, 54.87%, H, 6.48% N, 5.91%.

EXAMPLE 24

1,3-Dihydro-3-(2-chloro-2-methylpropyl)-2H-isoindol-1-one (I: $R^1$, $R^2$, $R^6$ and $R^7$=H, $R^3$ and $R^4$=Me, $R^5$=Cl and X=CO)

1,3-Dihydro-3-(2-hydroxy-2-methylpropyl)-2H-isoindol-1-one (12 g, described in Example 2) is added portionwise to thionyl chloride (72 ml) while stirring at room temperature. After 2 hr the reaction is evaporated and the residue is chromatographed on silica gel using acetone-toluene (3:7). The eluates are evaporated and crystallized from ethyl acetate-diethyl ether to give the title compound (2.2 g); mp 153°–155° C. and Anal. Calcd for C$_{12}$H$_{14}$ClNO: C, 64.43% H, 6.31% N, 6.27% and Found: 64.25% H, 6.26% N, 6.17%.

EXAMPLE 25

1,3-Dihydro-β,β-dimethyl-2H-isoindole-1-ethanol (I: $R^1$, $R^2$, $R^6$ and $R^7$=H, $R^3$ and $R^4$=Me, $R^5$=OH and X=CH$_2$)

A solution of 2,3-dihydro-3-(2-hydroxy-2-methylpropyl)-1H-isoindol-1-one (5 g, 0.024 mol, described in Example 2) in 240 ml of tetrahydrofuran is added dropwise to a solution of diborane in tetrahydrofuran (97.6 ml of IM BH$_3$/THF and 240 ml THF), and the solution is refluxed for 0.5 hr and cooled. Water is added to destroy the excess BH$_3$ and acidified with 6 N hydrochloric acid. Most of the solvent is evaporated off, and water is added. The solution is cooled to 5° C., made alkaline with 6 N sodium hydroxide and extracted with chloroform. The organic extract is dried and evaporated to afford 6.1 g of the title compound. The latter compound in diethyl ether is reacted with hydrogen chloride and the percipitate is collected and crystallized from isopropanol-diethyl ether to give the hydrochloride salt (3.7 g) of the title compound: mp 161°–163° C. and Anal. Calcd for C$_{12}$H$_{17}$NO.HCl: C, 63.29% H, 7.97% N, 6.15% and Found: C, 63.31% H, 7.96% N, 6.02%.

EXAMPLE 26

1,3-Dihydro-3-(2-hydroxypropyl)-2H-isoindol-1-one (I: $R^1$, $R^2$, $R^3$, $R^6$ and $R^7$=H, $R^4$=Me, $R^5$=OH and X=CO)

Methyl lithium (104 ml of 2.2 M in diethyl ether) is added dropwise to a solution at room temperature of 1,3-dihydro-1-oxo-2H-isoindole-1-acetic acid (10 g, described by F. M. Rowe et al., cited above) in dry tetrahydrofuran (600 ml). The solution is stirred for 3 hr and poured into cold 10% hydrochloric acid (200 ml). The solution is evaporated to about 200 ml and extracted with chloroform. The organic extract is washed with 5% aqueous sodium bicarbonate and water, dried and evaporated. The residue is chromatographed on silica gel using acetone-benzene (3:7) and the eluates are evaporated and crystallized from benzene-petroleum ether to give 5.0 g of 1,3-dihydro-3-oxo-2H-isoindol-1-propan-2'-one: mp 140°–142° C. and Anal. Calcd for C$_{11}$H$_{11}$NO$_2$: C, 69.82% H, 5.86% N, 7.4 and Found: C, 69.97% H, 5.95% N, 7.13% (A. Warshawsky and D. Ben-Ishai, cited above, reports mp 141°–142° C. for this compound).

Sodium borohydride (10 g, 0.26 mol) is added portionwise to a stirring solution of the latter ketone (10 g, 0.053 mol) in 500 ml of ethanol. This is stirred at reflux for 0.75 hr and evaporated. The residue is taken into water and extracted with chloroform. The combined chloroform extracts are washed with water, dried and evaporated to give 9.6 g of oil. Chromatography on silica gel using 45% acetone in benzene and evaporation of the eluates gives two fractions, A and B. Fraction A is crystallized from benzene-pentane to give isomer A (1.7 g containing 66% isomer A) of the title compound: mp 100°–102° C. and Anal. Calcd for C$_{11}$H$_{13}$NO$_2$: C, 69.09% H, 6.85% N, 7.32% and Found: C, 68.82% H, 6.77% N, 7.10%. Fraction B is crystallized from acetone-benzene to give isomer B (4.3 g containing 73% isomer B) of the title compound: mp 109°–112° C. and Anal. Found: C, 68.71% H, 6.74% N, 7.14%.

EXAMPLE 27

1,3-Dihydro-3-(2-methyl-1-propenyl)-2H-isoindol-1-one (I: $R^1$, $R^2$ and $R^7$=H, $R^3$ and $R^4$=Me, $R^5$ and $R^6$ together form a double bond and X=CO)

A solution consisting of 132 g concentrated sulfuric acid and 72 ml of glacial acetic acid is added dropwise to a stirring solution of 2,3-dihydro-3-(2-hydroxy-2-methylpropyl)-1H-isoindol-1-one (12 g, 0.058 mol, described in Example 2) in 84 ml of glacial acetic acid at 60° C. After stirring for 1 hr at this temperature the reaction is poured into 2 l. of crushed ice-water and extracted thrice with chloroform. The combined extracts are washed with 5% sodium bicarbonate and water, dried and evaporated to give 10.6 g of brown oil. Chromatography on silica gel using 30% acetone-toluene gives 6.4 g of solid. This is recrystallized from ethyl acetate-petroleum ether to afford 3.5 g of the title compound (thin layer chromatography on silica gel impregnated with silver perchlorate shows that is a mixture with 1,3-dihydro-3-(2-methyl-2-propenyl)-2H-isoindol-1-one): mp 123°–125° C. and Anal. Calcd for $C_{12}H_{13}NO$: C, 76.98% H, 7.00% N, 7.48% and Found: C, 76.63% H, 7.47%.

EXAMPLE 28

1,3-Dihydro-2,3-dimethyl-3-(2-hydroxy-2-methylpropyl)-2H-isoindol-1-one (I: $R^1$ and $R^6$=H, $R^2$, $R^3$, $R^4$ and $R^7$=Me, $R^5$=OH and X=CO)

Methyl iodide (13.2 g, 0.093 mol) is added to a string mixture of ethyl 1,3-dihydro-3-oxo-2H-isoindole-1-acetate (10 g, described in Example 1) and sodium hydride (2.18 g of a 50% dispersion, 0.045 mol) in 400 ml of benzene. This is stirred at 40°–50° C. for 5 hr. The reaction is cooled, made slightly acidic with 50% solution of acetic acid. Water is added and the phases are separated. The aqueous phase is extracted with benzene and the combined benzene extracts are dried and evaporated to give 13.1 g of oil. Chromatography on silica gel using 30% acetone in toluene affords 10.5 g of an oil of ethyl 1,3-dihydro-3-oxo-2-methyl-2H-isoindole-1-acetate, nmr ($CDCl_3$) δ 1.15 (t, 3H), 2.64 (d, 1H), 2.72 (d, 1H), 3.05 (s, 3H), 4.07 (q, 2H), 4.72 (t, 1H) and 7.35–7.65 (m, 4H).

The latter compound (10.0 g) in 545 ml of dry tetrahydrofuran is added dropwise to a stirring solution of methyl magnesium bromide (prepared from 5.2 g of magnesium and 31.8 g of methyl iodide) in 200 ml of dry diethyl ether. The reaction is stirred at reflux for 2 hr and then poured into 410 ml of cold 10% sulfuric acid. This is extracted with chloroform and the extract is washed with 5% sodium bicarbonate and water, dried and evaporated to give 3.9g of semisolid. Chromatography on silica gel using 50% acetone in toluene affords 2.5 g of oil that solidified on standing. This is crystallized from ethyl acetate to give 1.2 to give 1.2 g of white crystalline title compound: mp 105°–107° C., nmr ($CDCl_3$) δ 0.8 (s, 3H), 0.9 (s, 3H), 1.2 (s, 1H), 1.44 (s, 3H), 2.25 (s, 2H), 3.05 (s, 3H) and 7.45–7.75 (m, 4H); and Anal. Calcd for $C_{14}H_{19}NO_2$: C, 72.07% H, 8.21% N, 6.00% and Found: C, 71.96% H, 8.29% N, 5.83%.

EXAMPLE 29

Effect of a Compound of Formula I on Basal Gastric Acid in the Rat

Gastric acid secretion is measured essentially according to the method of H. Shay et al., Gastroenterol., 26, 906 (1954) as described by W. Lippmann, J. Pharm. Pharmacol., 22 568 (1970). Female sprague Dawley rats (Canadian Breeding Laboratories; 160–180 g) are fastened for 48 hours before pylorus ligation. After the first 24 hours of fasting the animals are given access to 8% sucrose in 0.2% sodium chloride for 8 hours. Water is permitted ad libitum except during the 8 hour access to sucrose and after the drug treatment. A compound of formula I is suspended in water with the aid of one drop of Tween 80 per 7 ml for oral administration. The pylorus is ligated under diethyl ether anesthesia and the sutured incision is covered with flexible collodion to prevent the animals from ingesting adhering blood. The stomachs are lavaged with 0.9% sodium chloride until the return solution is clear. Four hours after pylorus ligation, the animals are killed with diethyl ether and the gastric contents are collected in centrifuge tubes. The amount of acid in the centrifuged gastric juice is determined by tiration against 0.1 N sodium hydroxide in a direct reading pH meter to pH 7.0.

Atropine sulfate is obtained from May and Baker, Ltd.

Students "t" test is used in the evaluation of the data.

In this test, upon oral administration the following compounds of formula I inhibited gastric acid output: 7-chloro-1,3-dihydro-3-(2-hydroxy-2-methylpropyl)-2H-isoindol-1-one (described in Example 11) at a dose of 16.5 mg/kg causes 50% inhibition, 6-chloro-1,3-dihydro-3-(2-hydroxy-2-methylpropyl)-2H-isoindol-1-one (described in Example 11) at a dose of 100 mg/kg causes 53% inhibition, 5-chloro-1,3-dihydro-3-(2-hydroxy-2-methylpropyl)-2H-isoindol-1-one (described in Example 11) at a dose of 100 mg/kg causes 66% inhibition, 6-fluoro-1,3-dihydro-3-(2-hydroxy-2-methylpropyl)-2H-isoindol-1-one (described in Example 11) at a dose of 100 mg/kg causes 68% inhibition, 4-chloro-1,3-dihydro-3-(2-hydroxy-2-methylpropyl)-2H-isoindol-1-one (described in Example 22) at a dose of 100 mg/kg causes 45% inhibition, and 1,3-dihydro-3-(2-chloro-2-methylpropyl)-2H-isoindol-1-one (described in Example 24) at a dose of 100 mg/kg causes 86% inhibition.

We claim:

1. A compound of the formula

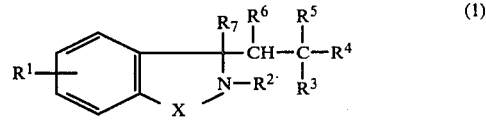

in which $R^1$ represents one or two substituents on the aromatic ring selected from hydrogen, lower alkyl, lower alkoxy, halo or trifluoromethyl; $R^2$ is hydrogen, lower alkyl or carboxymethyl; $R^3$ is hydrogen, lower alkyl or phenyl; $R^4$ is lower alkyl or phenyl; $R^5$ is bromo, chloro or hydroxy; $R^6$ is hydrogen or lower alkyl; $R^7$ is hydrogen or methyl and X is C=O; with the proviso that when $R^1$ represents one or two substituents at positions 5 and 6 on the aromatic ring; $R^2$, $R^6$ and $R^7$ are hydrogen; $R^3$ is hydrogen or lower alkyl and $R^4$ is lower alkyl; then $R^5$ is bromo or chloro.

2. A compound of claim 1 in which $R^1$ represents one or two substituents on the aromatic ring selected from hydrogen, lower alkyl, lower alkoxy or halo; $R^2$ is hydrogen, lower alkyl or carboxymethyl; $R^3$ is hydrogen, lower alkyl or phenyl; $R^4$ is lower alkyl or phenyl; $R^5$ is bromo, chloro or hydroxy; $R^6$ is hydrogen or lower alkyl; $R^7$ is hydrogen or methyl and X is C=O; with the proviso that when $R^1$ represents one or two substituents at positions 5 and 6 on the aromatic ring; $R^2$, $R^6$ and $R^7$ are hydrogen; $R^3$ is hydrogen or lower alkyl and $R^4$ is lower alkyl; then $R^5$ is bromo or chloro.

3. A compound of claim 1 in which $R^1$ represents one or two substituents on the aromatic ring selected from hydrogen or halo; $R^2$, $R^6$ and $R^7$ are hydrogen; $R^3$ is hydrogen or lower alkyl having one to three carbon atoms; $R^4$ is lower alkyl having one to three carbon atoms; $R^5$ is chloro or hydroxy and X is C=O; with the proviso that when $R^1$ represents one or two substituents at positions 5 and 6on the aromatic ring then $R^5$ is chloro.

4. 1,3-Dihydro-3-(2-hydroxy-2,2-diphenylethyl)-2H-isoindol-1-one, a compound of claim 1 in which $R^1$, $R^2$, $R^6$ and $R^7$ are hydrogen, $R^3$ and $R^4$ are phenyl, $R^5$ is hydroxy and X is CO.

5. 1,3-Dihydro-3-(2-hydroxy-2-methylpropyl)-1-oxo-isoindole-2-acetic acid, a compound of claim 1 in which $R^1$, $R^6$ and $R^7$ are hydrogen, $R^2$ is carboxymethyl, $R^3$ and $R^4$ are methyl, $R^5$ is hydroxy and X is CO.

6. 7-Chloro-1,3-dihydro-3-(2-hydroxy-2-methylpropyl)-2H-isoindol-1-one, a compound of claim 1 in which $R^1$ is 7-chloro, $R^2$, $R^6$ and $R^7$ are hydrogen, $R^3$ and $R^4$ are methyl, $R^5$ is hydroxy and X is CO.

7. 1,3-Dihydro-3-(2-hydroxy-2-methylpropyl)-7-methoxy-2H-isoindol-1-one, a compound of claim 1 in which $R^1$ is 7-methoxy, $R^2$, $R^6$ and $R^7$ are hydrogen, $R^3$ and $R^4$ are methyl, $R^5$ is hydroxy and X is CO.

8. 7-Bromo-1,3-dihydro-3-(2-hydroxy-2-methylpropyl)-2H-isoindol-1-one, a compound of claim 1 in which $R^1$ is 7-bromo, $R^2$, $R^6$ and $R^7$ are hydrogen, $R^3$ and $R^4$ are methyl, $R^5$ is hydroxy and X is CO.

9. 1,3-Dihydro-2-(1-methylethyl)-3-(2-hydroxy-2-methylpropyl)-2H-isoindol-1-one, a compound of claim 1 in which $R^1$, $R^6$ and $R^7$ are hydrogen, $R^2$ is 1-methylethyl, $R^3$ and $R^4$ are methyl, $R^5$ is hydroxy and X is CO.

10. 2-Ethyl-1,3-dihydro-3-(2-hydroxy-2-methylpropyl)-2H-isoindol-1-one, a compound of claim 1 in which $R^1$, $R^6$ and $R^7$ are hydrogen, $R^2$ is ethyl, $R^3$ and $R^4$ are methyl, $R^5$ is hydroxy and X is CO.

11. 4-Chloro-1,3-dihydro-3-(2-hydroxy-2-methylpropyl)-2H-isoindol-1-one, a compound of claim 1 in which $R^1$ is 4-Chloro, $R^2$, $R^6$ and $R^7$ are hydrogen, $R^3$ and $R^4$ are methyl, $R^5$ is hydroxy and X is CO.

12. 7-Bromo-1,3-dihydro-3-(2-hydroxy-2-methylpropyl)-4-methoxy-2H-isoindol-1-one, a compound of claim 1 in which $R^1$ is 7-bromo and 4-methoxy, $R^2$, $R^6$ and $R^7$ are hydrogen, $R^3$ and $R^4$ are methyl, $R^5$ is hydroxy and X is CO.

13. 1,3-Dihydro-3-(2-hydroxy-2-methylpropyl)-7-methyl-2H-isoindol-1-one, a compound of claim 1 in which $R^1$ is 7-methyl, $R^2$, $R^6$ and $R^7$ are hydrogen, $R^3$ and $R^4$ are methyl, $R^5$ is hydroxy and X is CO.

14. [3S[3α(S,S)]]-1,3-Dihydro-3-(3-hydroxy-3-methyl-2-butyl)-2H-isoindol-1-one, a compound of claim 1 in which $R^1$, $R^2$ and $R^7$ are hydrogen, $R^3$, $R^4$ and $R^6$ are methyl, $R^5$ is hydroxy and X is CO.

15. [3R[3α(R,R)]]-1,3-Dihydro-3-(3-hydroxy-3-methyl-2-butyl)-2H-isoindol-1-one, a compound of claim 1 in which $R^1$, $R^2$ and $R^7$ are hydrogen, $R^3$, $R^4$ and $R^6$ are methyl, $R^5$ is hydroxy and X is CO.

16. 1,3-Dihydro-3-(2-hydroxy-2-methylpropyl)-4-methoxy-2H-isoindol-1-one, a compound of claim 1 in which $R^1$ is 4-methoxy, $R^2$, $R^6$ and $R^7$ are hydrogen, $R^3$ and $R^4$ are methyl, $R^5$ is hydroxy and X is CO.

17. 1,3-Dihydro-3-(2-chloro-2-methylpropyl)-2H-isoindol-1-one, a compound of claim 1 in which $R^1$, $R^2$, $R^6$ and $R^7$ are hydrogen, $R^3$ and $R^4$ are methyl, $R^5$ is chloro and X is CO.

18. 1,3-Dihydro-2,3-dimethyl-3-(2-hydroxy-2-methylpropyl)-2H-isoindol-1-one, a compound of claim 1 in which $R^1$ and $R^6$ are hydrogen, $R^2$, $R^3$, $R^4$ and $R^7$ are methyl, $R^5$ is hydroxy and X is CO.

19. A method of treating ulcers in a mammal, which comprises orally administering to said mammal an effective ulcer alleviating amount of a compound of the formula

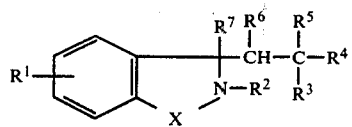

in which $R^1$ represents one or two substituents on the aromatic ring selected from hydrogen, lower alkyl, lower alkoxy, halo or trifluoromethyl; $R^2$ is hydrogen, lower alkyl or carboxymethyl; $R^3$ is hydrogen, lower alkyl or phenyl; $R^4$ is lower alkyl or phenyl; $R^5$ is bromo, chloro or hydroxy; $R^6$ is hydrogen or lower alkyl; $R^7$ is hydrogen or methyl and X is C=O; with the proviso that when $R^1$, $R^2$, $R^6$ and $R^7$ are hydrogen, $R^3$ and $R^4$ are methyl, then $R^5$ is bromo or chloro.

20. A method for preventing or decreasing the secretion of availability of excessive amounts of gastric acid in a mammal, which comprises orally administering to said mammal suffering from hyperchlorhydria an effective amount of a compound of the formula

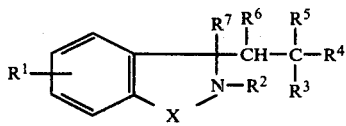

in which $R^1$ represents one or two substituents on the aromatic ring selected from hydrogen, lower alkyl, lower alkoxy, halo or trifluoromethyl; $R^2$ is hydrogen lower alkyl or carboxymethyl; $R^3$ is hydrogen, lower alkyl or phenyl; $R^4$ is lower alkyl or phenyl; $R^5$ is bromo, chloro, or hydroxy; $R^6$ is hydrogen or lower alkyl; $R^7$ is hydrogen or methyl and X is C=O; with the proviso that when $R^1$, $R^2$, $R^6$ and $R^7$ are hydrogen, $R^3$ and $R^4$ are methyl, then $R^5$ is bromo or chloro.

21. A pharmaceutical composition for treating hyperchlorhydria which comprises an effective amount of a compound of the formula

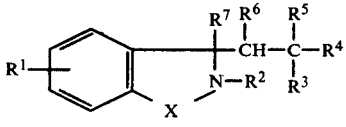

in which $R^1$ represents one or two substituents on the aromatic ring selected from hydrogen, lower alkyl, lower alkoxy, halo or trifluoromethyl; $R^2$ is hydrogen, lower alkyl or carboxymethyl; $R^3$ is hydrogen, lower alkyl or phenyl; $R^4$ is lower alkyl or phenyl; $R^5$ is bromo, chloro or hydroxy; $R^6$ is hydrogen or lower alkyl; $R^7$ is hydrogen or methyl and X is C=O; with the proviso that when $R^1$, $R^2$, $R^6$ and $R^7$ are hydrogen, $R^3$ and $R^4$ are methyl and X is C=O, then $R^5$ is bromo or chloro; and a pharmaceutically acceptable carrier therefor.

* * * * *